US008706455B2

(12) United States Patent
Van Beurden et al.

(10) Patent No.: US 8,706,455 B2
(45) Date of Patent: Apr. 22, 2014

(54) METHODS AND APPARATUS FOR CALCULATING ELECTROMAGNETIC SCATTERING PROPERTIES OF A STRUCTURE USING A NORMAL-VECTOR FIELD AND FOR RECONSTRUCTION OF APPROXIMATE STRUCTURES

(75) Inventors: Martijn Constant Van Beurden, Eindhoven (NL); Irwan Dani Setija, Utrecht (NL); Remco Dirks, Deurne (NL)

(73) Assignee: ASML Netherlands B.V., Veldhoven (NL)

( * ) Notice: Subject to any disclaimer, the term of this patent is extended or adjusted under 35 U.S.C. 154(b) by 475 days.

(21) Appl. No.: 12/905,447

(22) Filed: Oct. 15, 2010

(65) Prior Publication Data

US 2011/0098992 A1 Apr. 28, 2011

Related U.S. Application Data

(60) Provisional application No. 61/272,690, filed on Oct. 22, 2009, provisional application No. 61/354,825, filed on Jun. 15, 2010.

(51) Int. Cl.
*G06F 7/60* (2006.01)
*G06G 7/56* (2006.01)
*G06G 7/48* (2006.01)

(52) U.S. Cl.
USPC ........................................ 703/5; 703/2; 703/6

(58) Field of Classification Search
None
See application file for complete search history.

(56) References Cited

U.S. PATENT DOCUMENTS

| | | | |
|---|---|---|---|
| 6,377,041 B1 * | 4/2002 | Jones et al. | 324/244 |
| 6,847,925 B2 * | 1/2005 | Ottusch et al. | 703/2 |
| 6,867,866 B1 | 3/2005 | Chang et al. | |
| 7,038,850 B2 * | 5/2006 | Chang et al. | 359/446 |
| 7,710,572 B2 * | 5/2010 | Mos et al. | 356/448 |
| 2005/0185174 A1 | 8/2005 | Laan et al. | |
| 2008/0069430 A1 * | 3/2008 | Setija et al. | 382/144 |

FOREIGN PATENT DOCUMENTS

EP 1 628 164 A2 2/2006

OTHER PUBLICATIONS

Schuster, T., et al., "Normal vector method for convergence improvement using the RCWA for crossed gratings", *J. Opt. Soc. Am. A*, 24(9):2880-2890, Optical Society of America, United States (2007).

(Continued)

*Primary Examiner* — Omar Fernandez Rivas
*Assistant Examiner* — Nithya J Moll
(74) *Attorney, Agent, or Firm* — Sterne, Kessler, Goldstein & Fox P.L.L.C

(57) ABSTRACT

A projection operator framework is described to analyze the concept of localized normal-vector fields within field-material interactions in a spectral basis, in isotropic and anisotropic media. Generate a localized normal-vector field n in a region of the structure defined by the material boundary, decomposed into sub-regions with a predefined normal-vector field and possibly corresponding closed-form integrals. Construct a continuous vector field F using the normal-vector field to select continuous components $E_T$ and $D_n$. Localized integration of normal-vector field n over the sub-regions to determine coefficients of, C. Determine components $E_x$, $E_y$, $E_z$ of the electromagnetic field by using field-material interaction operator C to operate on vector field F. Calculate electromagnetic scattering properties of the structure using the determined components of the electromagnetic field.

29 Claims, 18 Drawing Sheets

(56) References Cited

OTHER PUBLICATIONS

International Search Report and the Written Opinion of the International Searching Authority directed to related International application No. PCT/EP2010/065457 mailed Jan. 20, 2011, European Patent Office, Rijswijk, Netherlands; 22 pages.

Bergner, B. C., "Effect of Line Width Roughness on Optical Scatterometry Measurements", Proceedings of the SPIE, Metrology, Inspection, and Process Control for Microlithography XXIII, vol. 7272, 2009; 8 pages.

Chang, Y.-C., et al., "Efficient finite-element, Green's function approach for critical-dimension metrology of three-dimensional gratings on multilayer films", Journal of the Optical Society of America A., vol. 23, No. 3, Mar. 2006; pp. 638-645.

Gabard, G., "Exact integration of polynomial-exponential products with application to wave-based numerical methods", Communications in Numerical Methods in Engineering, Vo. 25, No. 3, Mar. 2008; pp. 237-246.

Götz, P., et al., "Normal vector method for the RCWA with automated vector field generation", Optics Express, vol. 16, No. 22, Oct. 2008; pp. 17295-17301.

Li, L., "New formulation of the Fourier modal method for crossed surface-relief gratings", Journal of the Optical Society of America A, vol. 14, No. 19, Oct. 1997; pp. 2758-2767.

Li, L., "Use of Fourier series in the analysis of discontinuous periodic structures", Journal of the Optical Society of America A, vol. 13, No. 9, Sep. 1996a; pp. 1870-1876.

Popov, E., et al., "Maxwell equations in Fourier space: fast-converging formulation for diffraction by arbitrary shaped, periodic, anisotropic media", Journal of the Optical Society of America A, vol. 18a, No. 11, Nov. 2001; pp. 2886-2894.

Sommariva, A., et al., "Gauss-Green cubature and moment computation over arbitrary geometries", University of Padua, Department of Pure and Applied Mathematics, Mar. 2009; 18 pages.

Sommariva, A., et al., "Product Gauss cubature over polygons based on Green's integration formula", BIT Numerical Mathematics, vol. 47, No. 2, Aug. 2007; 13 pages.

Churchill, R.V., "Complex Variables and Applications," Second Edition, McGraw-Hill Book Company, 1960.

Gradshteyn, I.S., et al., "Table of Integrals, Series and Products," Corrected and Enlarged Edition, Academic Press, Inc., 1980.

\* cited by examiner

METHODS AND APPARATUS FOR CALCULATING ELECTROMAGNETIC SCATTERING PROPERTIES OF A STRUCTURE USING A NORMAL-VECTOR FIELD AND FOR RECONSTRUCTION OF APPROXIMATE STRUCTURES

CROSS REFERENCE TO RELATED APPLICATIONS

This application is claims the benefit under 35 U.S.C. §119(e) to U.S. Provisional Patent Application Nos. 61/354,825, filed Jun. 15, 2010, and 61/272,690, filed Oct. 22, 2009, which are incorporated by reference herein in their entireties.

FIELD

The present invention relates to calculation of electromagnetic scattering properties of periodic structures using a normal-vector field. The invention may be applied for example in metrology of microscopic structures, for example to assess critical dimensions (CD) performance of a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

More generally, it would be useful to be able to compare the scattered radiation with scattering behaviors predicted mathematically from models of structures, which can be freely set up and varied until the predicted behavior matches the observed scattering from a real sample. Unfortunately, although it is in principle known how to model the scattering by numerical procedures, the computational burden of the known techniques renders such techniques impractical, particularly if real-time reconstruction is desired, and/or where the structures involved are more complicated than a simple structure periodic in one-dimension.

SUMMARY

It is desirable in the field of semiconductor processing to rapidly perform accurate calculations of electromagnetic scattering properties of periodic structures.

According to a first aspect of the invention, there is provided a method of calculating electromagnetic scattering properties of a structure, the structure including materials of differing properties such as to cause a discontinuity in an electromagnetic field at a material boundary, the method comprising: generating a localized normal-vector field in a region of the structure defined with reference to the material boundary, constructing a vector field that is continuous at the material boundary by using the normal-vector field to select continuous components of the electromagnetic field tangential to the material boundary and to select continuous components of a corresponding electromagnetic flux density normal to the material boundary, performing a localized integration of the normal-vector field over the region to determine coefficients of a field-material interaction operator, numerically determining a component of the electromagnetic field by using the field-material interaction operator to operate on the vector field, and calculating electromagnetic scattering properties of the structure using the determined component of the electromagnetic field.

According to a second aspect of the invention, there is provided a method of reconstructing an approximate structure of an object from a detected electromagnetic scattering property arising from illumination of the object by radiation, the method comprising the steps: estimating at least one structural parameter, determining at least one model electromagnetic scattering property from the at least one structural parameter, comparing the detected electromagnetic scattering property to the at least one model electromagnetic scattering property, and determining an approximate object structure based on the result of the comparison, wherein the model electromagnetic scattering property is determined using a method according to the first aspect.

According to a third aspect of the invention, there is provided an inspection apparatus for reconstructing an approximate structure of an object, the inspection apparatus comprising: an illumination system configured to illuminate the object with radiation, a detection system configured to detect an electromagnetic scattering property arising from the illumination: a processor configured to: estimate at least one structural parameter, determine at least one model electromagnetic scattering property from the at least one structural parameter, compare the detected electromagnetic scattering property to the at least one model electromagnetic scattering property, and determine an approximate object structure from a difference between the detected electromagnetic scattering property and the at least one model electromagnetic scattering property, wherein the processor is configured to determine the model electromagnetic scattering property using a method according to the first aspect.

According to a fourth aspect of the invention, there is provided a computer program product containing one or more sequences of machine-readable instructions for calculating electromagnetic scattering properties of a structure, the instructions being adapted to cause one or more processors to perform a method according to the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
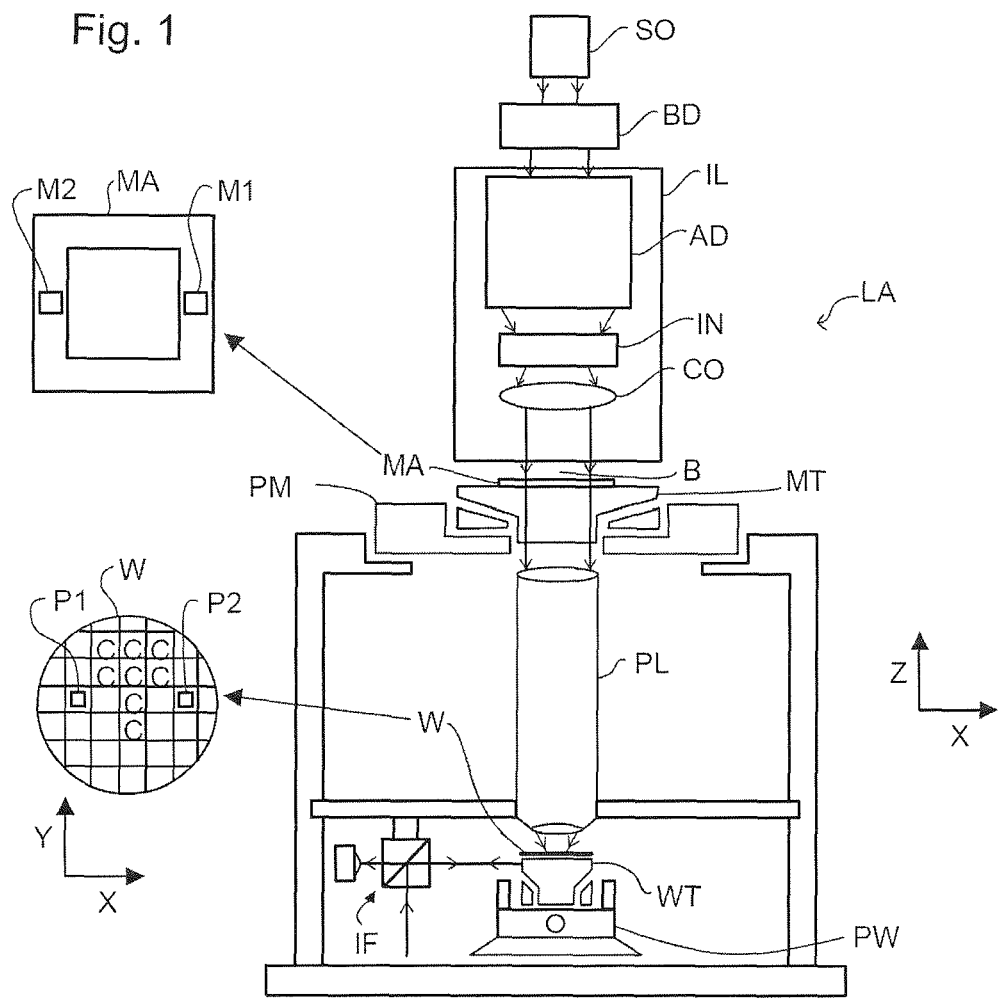
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises: an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is-reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. -An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
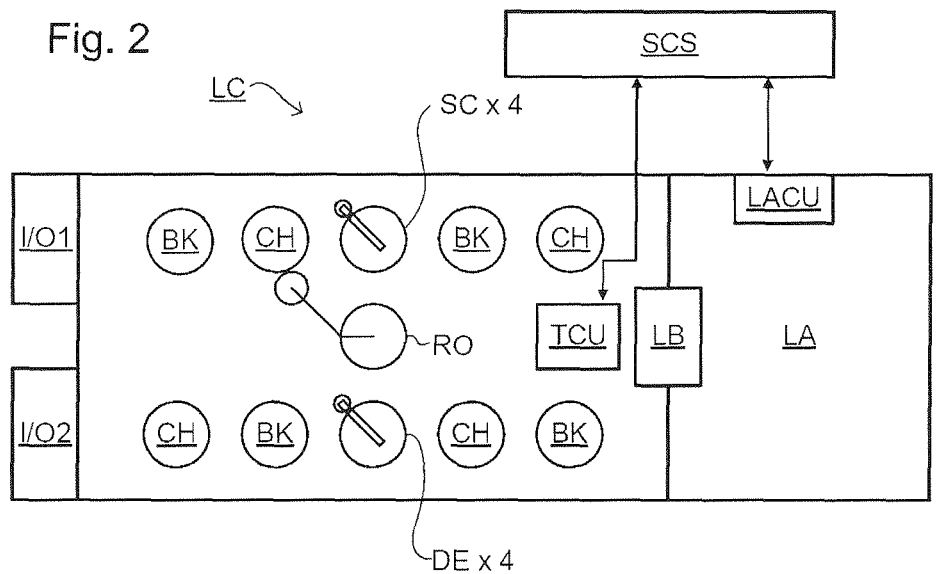
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
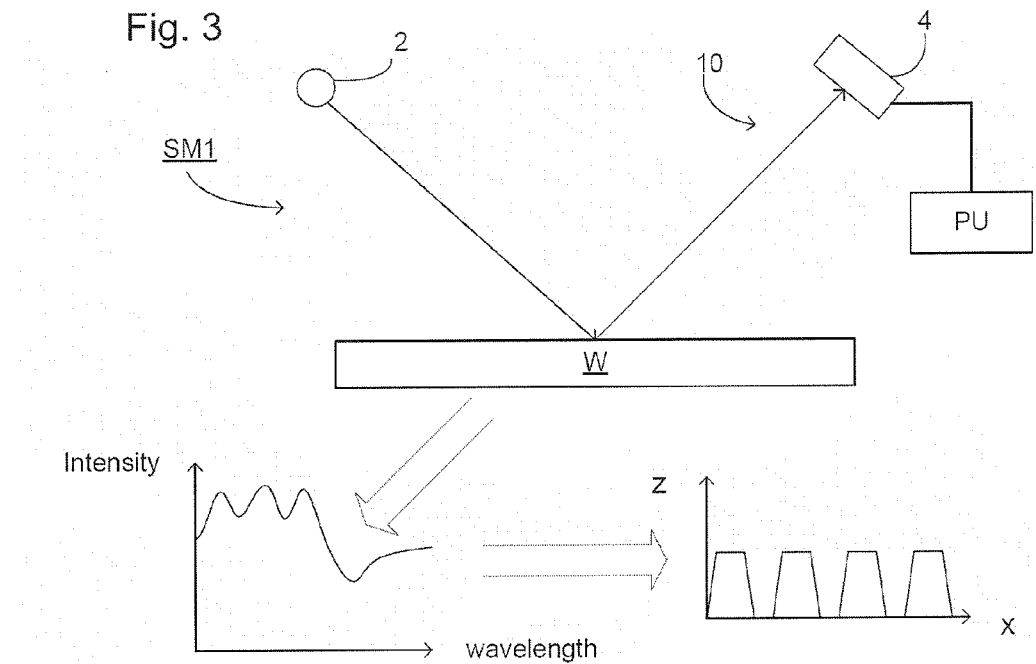
FIG. 3 depicts a first scatterometer.

FIG. 3 depicts a scatterometer which may be used in an embodiment of the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., conventionally by Rigorous Coupled Wave Analysis (RCWA) and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
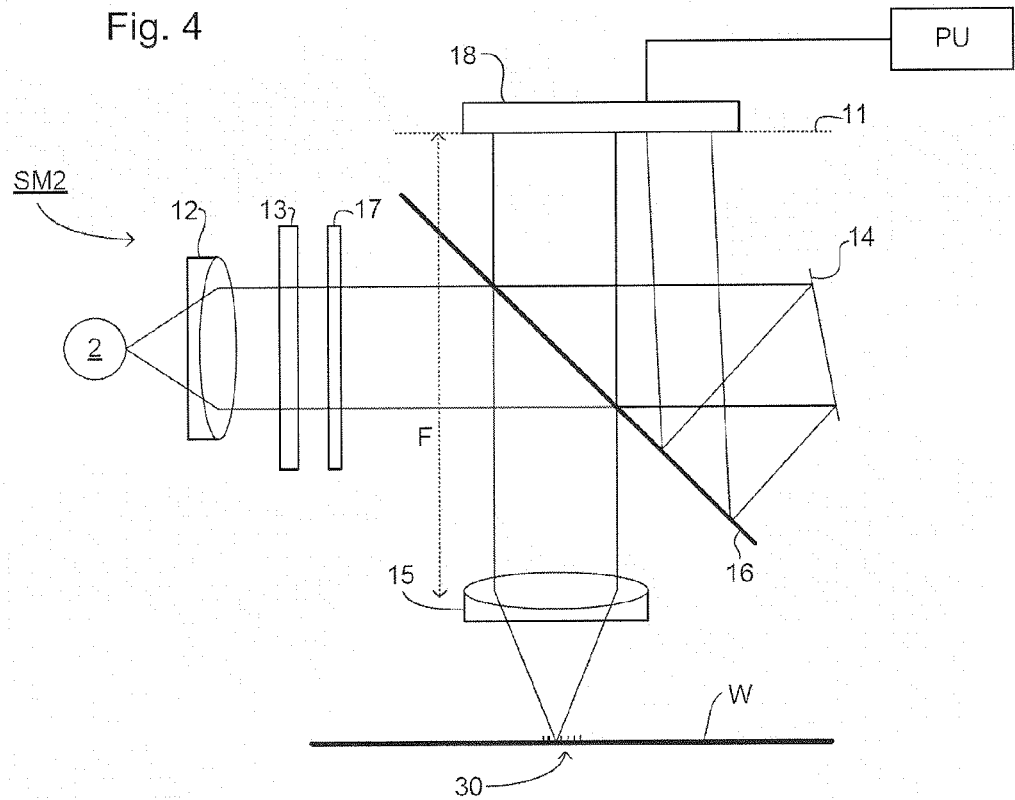
FIG. 4 depicts a second scatterometer.

Another scatterometer that may be used in an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least $2\Delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Modelling

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
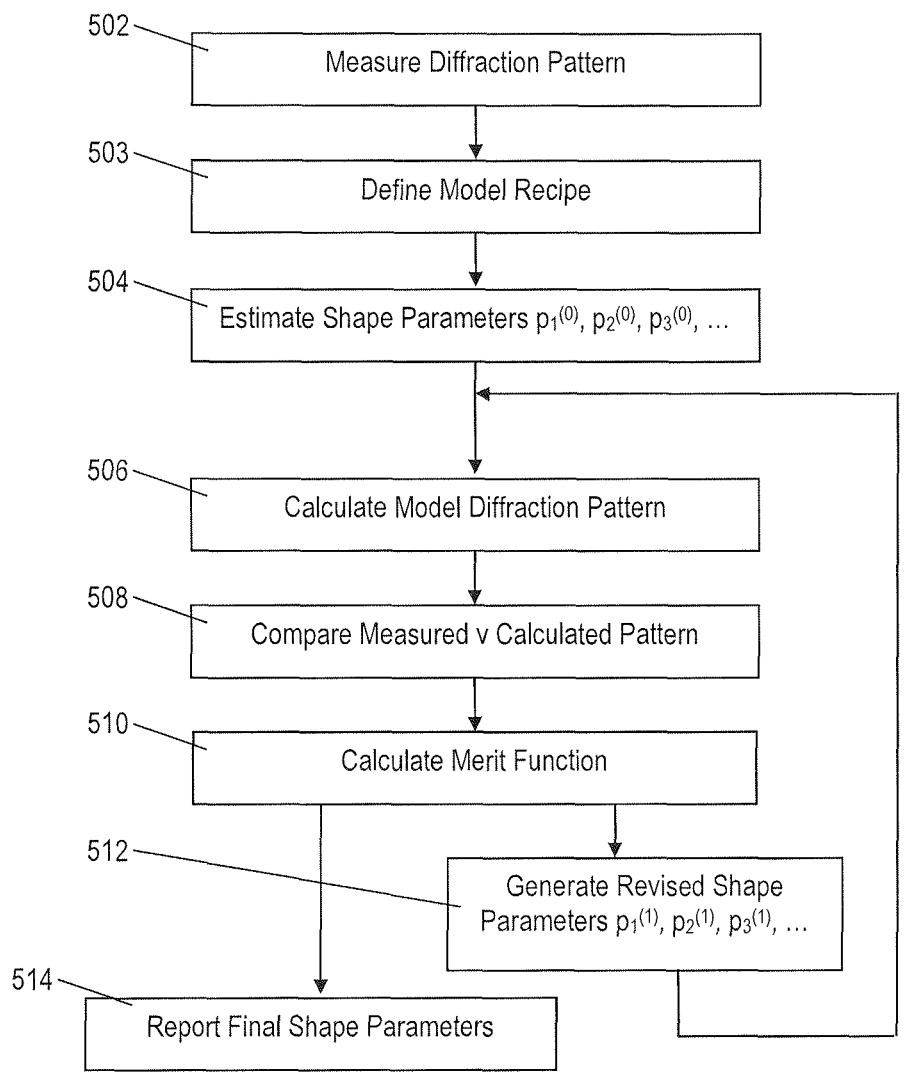
FIG. 5 depicts a first example process using an embodiment of the invention for reconstruction of a structure from scatterometer measurements.

Referring to FIG. 5 in more detail, the way the measurement of the target shape and/or material properties is carried out will be described in summary. The target will be assumed for this description to be a 1-dimensional (1-D) structure. In practice it may be 2-dimensional, and the processing will be adapted accordingly.

In step 502, the diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503, a 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$.

In step 504: A model target shape is estimated by setting initial values $p_i^{(0)}$ for the floating parameters (i.e. $p_1^{(0)}$, $p_2^{(0)}$, $p_3^{(0)}$ and so on). Each floating parameter will be generated within certain predetermined ranges, as defined in the recipe.

In step 506, the parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508 and 510, the measured diffraction pattern and the model diffraction pattern are then compared and their similarities and differences are used to calculate a "merit function" for the model target shape.

In step 512, assuming that the merit function indicates that the model needs to be improved before it represents accurately the actual target shape, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514, when the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom.

The estimated or model diffraction pattern calculated at 506 can be expressed in various forms. Comparisons are simplified if the calculated pattern is expressed in the same form as the measured pattern generated in step 510. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
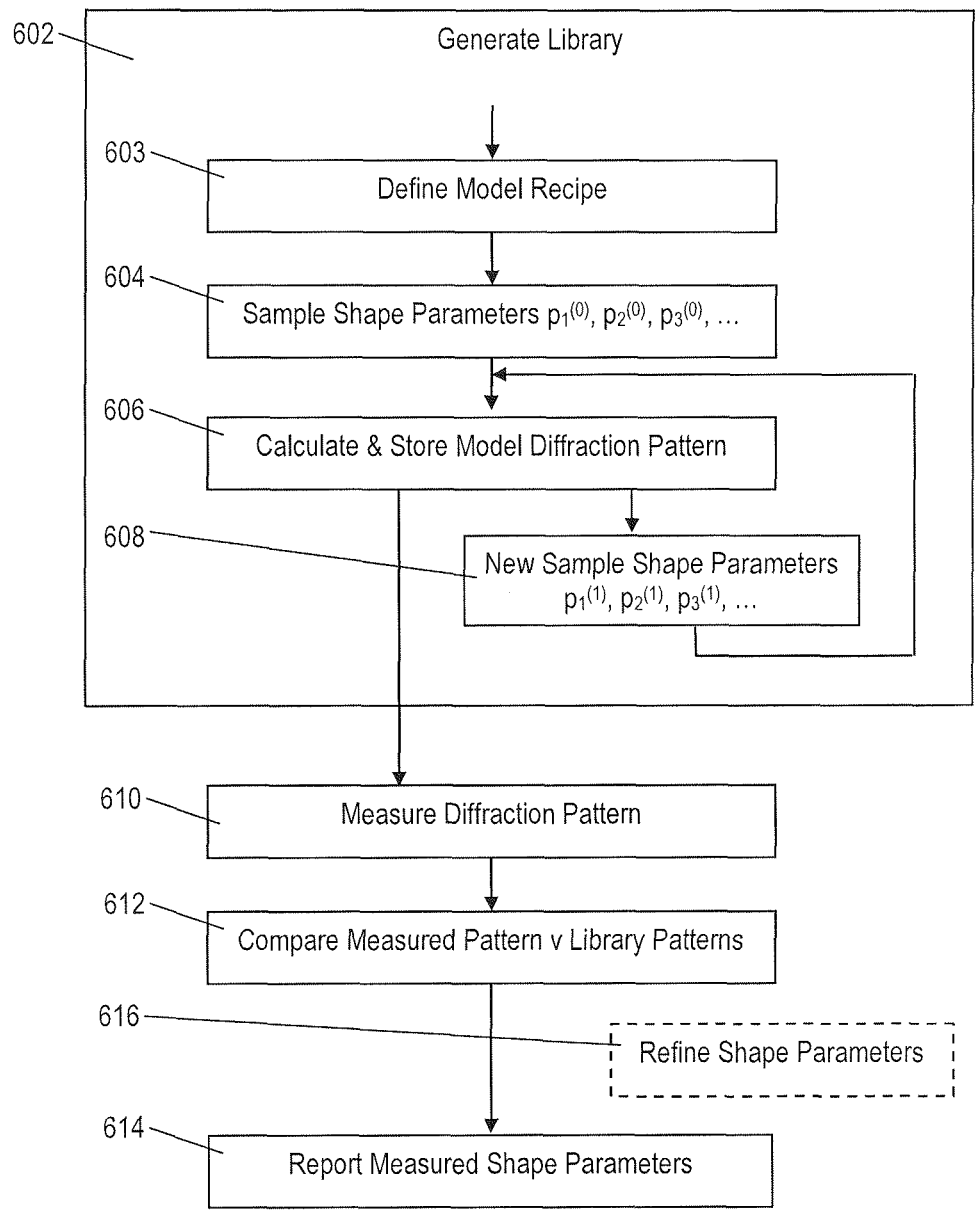
FIG. 6 depicts a second example process using an embodiment of the invention for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602, the process of generating the library is performed. A separate library may be generated for each type of target structure. The library may be generated by a user of the measurement apparatus according to need, or may be pre-generated by a supplier of the apparatus.

In step 603, a 'model recipe' is established which defines a parameterized model of the target structure in terms of a number of parameters $p_i$ ($p_1$, $p_2$, $p_3$ and so on). Considerations are similar to those in step 503 of the iterative process.

In step 604, a first set of parameters $p_1^{(0)}$, $p_2^{(0)}$, $p_3^{(0)}$, etc. is generated, for example by generating random values of all the parameters, each within its expected range of values.

In step 606, a model diffraction pattern is calculated and stored in a library, representing the diffraction pattern expected from a target shape represented by the parameters.

In step 608, a new set of shape parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610, after the library is generated (though it could be before), the real target 30 is placed in the scatterometer and its diffraction pattern is measured.

In step 612, the measured pattern is compared with the modeled patterns stored in the library to find the best matching pattern. The comparison may be made with every sample in the library, or a more systematic searching strategy may be employed, to reduce computational burden.

In step 614, if a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616, optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e. the calculation of the estimated model diffraction pattern using a rigorous optical diffraction theory from the estimated target shape.

For CD reconstruction of 2D-periodic structures RCWA is commonly used in the forward diffraction model, while the Differential Method, the Volume Integral Method (VIM), Finite-difference time-domain (FDTD), and Finite element method (FEM) have also been reported.

RCWA

Figure 7A:
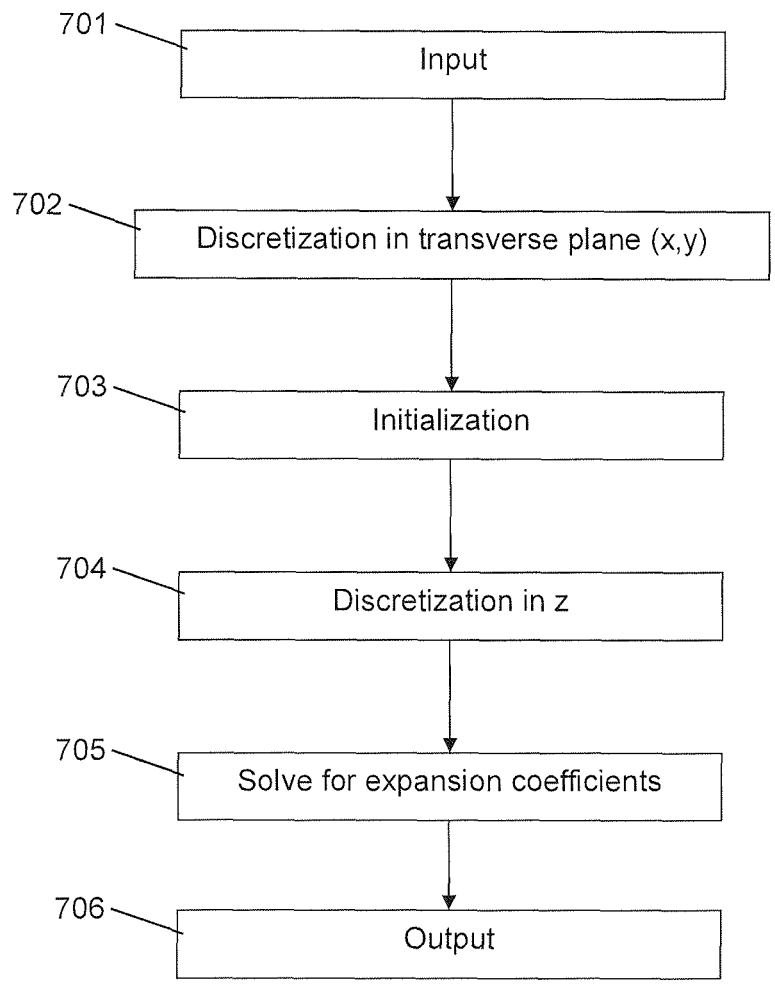
FIG. 7a is a flowchart of the Rigorous Coupled Wave Analysis (RCWA) method of calculating electromagnetic scattering properties of a structure.

FIG. 7a is a flowchart of the RCWA method of calculating electromagnetic scattering properties of a structure. The following steps are depicted.

In step 701: Input: Specify geometrical setup, material distribution, and incident field In step 702: Discretization in transverse plane (x,y):
  Set up normal-vector field for each layer, taking into account all the material boundaries and compute the Fourier transforms of this normal-vector field
  Determine Fourier transforms of the permittivity and inverse permittivity for each layer In step 703: Initialization:
  Set up Toeplitz matrices with Fourier coefficients (previous step) for each layer for the normal-vector field, the permittivity, and inverse permittivity
  Compute the inverse of the inverse permittivity matrices for each layer
  Compose (multiply and add) the above matrices to form the total field-material interaction matrices for each layer
  Set up matrices with wave vector components $k_x$, $k_y$, $k_{1z}$, $k_{2z}$ In step 704: Discretization in z: Solve eigenvalue system for each layer using matrices from previous step In step 705: Solve for expansion coefficients:
  Set up sparse linear system that matches the boundary conditions and use block LU or alternative method, or
  Use stable condensation algorithm to solve sparse linear system, which typically results in a forward and backward recursive algorithm involving Riccati matrices or scattering matrices

706: Output: Typically compute reflection coefficients and/or diffraction efficiencies from obtained expansion coefficients Differential Method FIG. 7b is a flowchart of the differential method of method of calculating electromagnetic scattering properties of a structure.

Figure 7B:
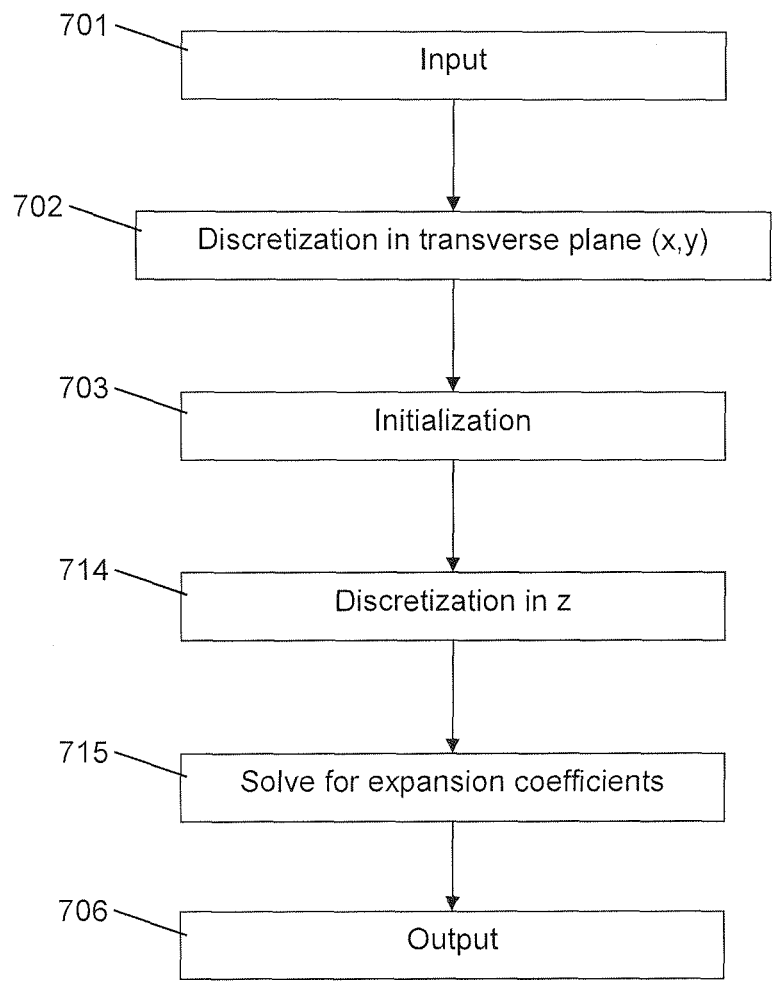
FIG. 7b is a flowchart of the differential method of calculating electromagnetic scattering properties of a structure.

With reference to FIG. 7b, the flowchart of the differential method is identical to RCWA for steps 701, 702, 703, and 706. After step 703, a system of first order differential equations in the z-direction is obtained. As discussed above, RCWA then solves the system per layer via an eigenvalue decomposition and then matches the fields at the interfaces between the layers. In the differential method, the differential equation together with a set of boundary conditions is solved. There are several ways to solve the pertaining boundary value problem:

Shooting: in step 714, the system of boundary conditions is formulated and the differential equation is integrated via a shooting method. Step 705 can be left out. This method is almost always unstable.

Multiple shooting: step 714 contains the formulation of the boundary conditions for each layer and the numerical integration of the boundary value problem for each layer. In step 715, the fields at the connecting interfaces between the layers are matched, similarly to RCWA.

Stabilized march: again step 714 contains the set up of the boundary conditions for (sub)layer. Then an orthogonalization step, followed by integration of the differential equation on the orthogonalized basis. This process of orthogonalization and integration travels sequentially along the stack of (sub)layers. In this case, the steps 714 and 715 can no longer be separated.

Normal-Vector Fields

In rigorous diffraction modeling it has been demonstrated [1] that convergence of the solution can be drastically improved by introducing an auxiliary intermediate field F that is continuous across material interfaces instead of the E- and D-fields that have discontinuous components across these interfaces. Improved convergence leads to more accurate answers at less computational cost, one of the major challenges in optical scatterometry, in particular for 2D-periodic diffraction gratings.

This vector field F is formulated using a so-called normal-vector field, a fictitious vector field that is perpendicular to the material interface. Algorithms to generate normal-vector fields have been proposed in [3,5], within the context of RCWA. Normal-vector fields have been used not only in combination with RCWA, but also in combination with the Differential Method.

However, one of the major difficulties of the normal-vector field concept is the actual generation of the normal-vector field itself over the entire domain of computation. There are very few constraints to generate such field, but at the same time there are many open questions related to its generation. The normal-vector field must be generated for the full geometrical setup and one cannot operate on isolated domains without taking care of connecting material interfaces. Solutions have been proposed using Schwartz-Christoffel transformations [3], but all these methods suffer from either a lack of flexibility to generate normal-vector fields for arbitrary shapes or a flexibility that comes at a high computational cost [5]. Both are devastating for fast reconstruction since for a reconstruction it is important to keep track of a continuously varying normal-vector field under varying dimensions of a grating structure. This is important because a discontinuously evolving normal-vector field may disrupt the convergence of the overall nonlinear solver that guides the reconstruction process. A further issue is the time required to set up a normal-vector field. This computational overhead should be as low as possible, to allow for fast analysis and reconstruction.

Volume Integral Method

One of the major problems of RCWA is that it requires a large amount of central processing unit (CPU) time and memory for 2D periodic structures, since a sequence of eigenvalue/eigenvector problems need to be solved and concatenated. For FDTD and FEM, CPU time is typically also too high.

Known Volume Integral Methods (as disclosed in [9], U.S. Pat. No. 6,867,866 B1 and U.S. Pat. No. 7,038,850 B2) are based either on fully spatial discretization schemes that exhibit slow convergence with respect to mesh refinement or on spectral discretization schemes that exhibit poor convergence with respect to an increasing number of harmonics. As an alternative, a spectral discretization scheme that incorporates a heuristic method to improve the convergence has been proposed [9].

The linear system that has to be solved for VIM is much larger compared to RCWA, but if it is solved in an iterative way, only the matrix-vector product is needed together with the storage of several vectors. Therefore, the memory usage is typically much lower than for RCWA. The potential bottleneck is the speed of the matrix-vector product itself. If the Li rules [10, 11] were to be applied in VIM, then the matrix-vector product would be much slower, due to the presence of several inverse sub-matrices. Alternatively, the Li rules can be ignored and FFTs can be used to arrive at a fast matrix-vector product, but the problem of poor convergence remains.

Figure 8:
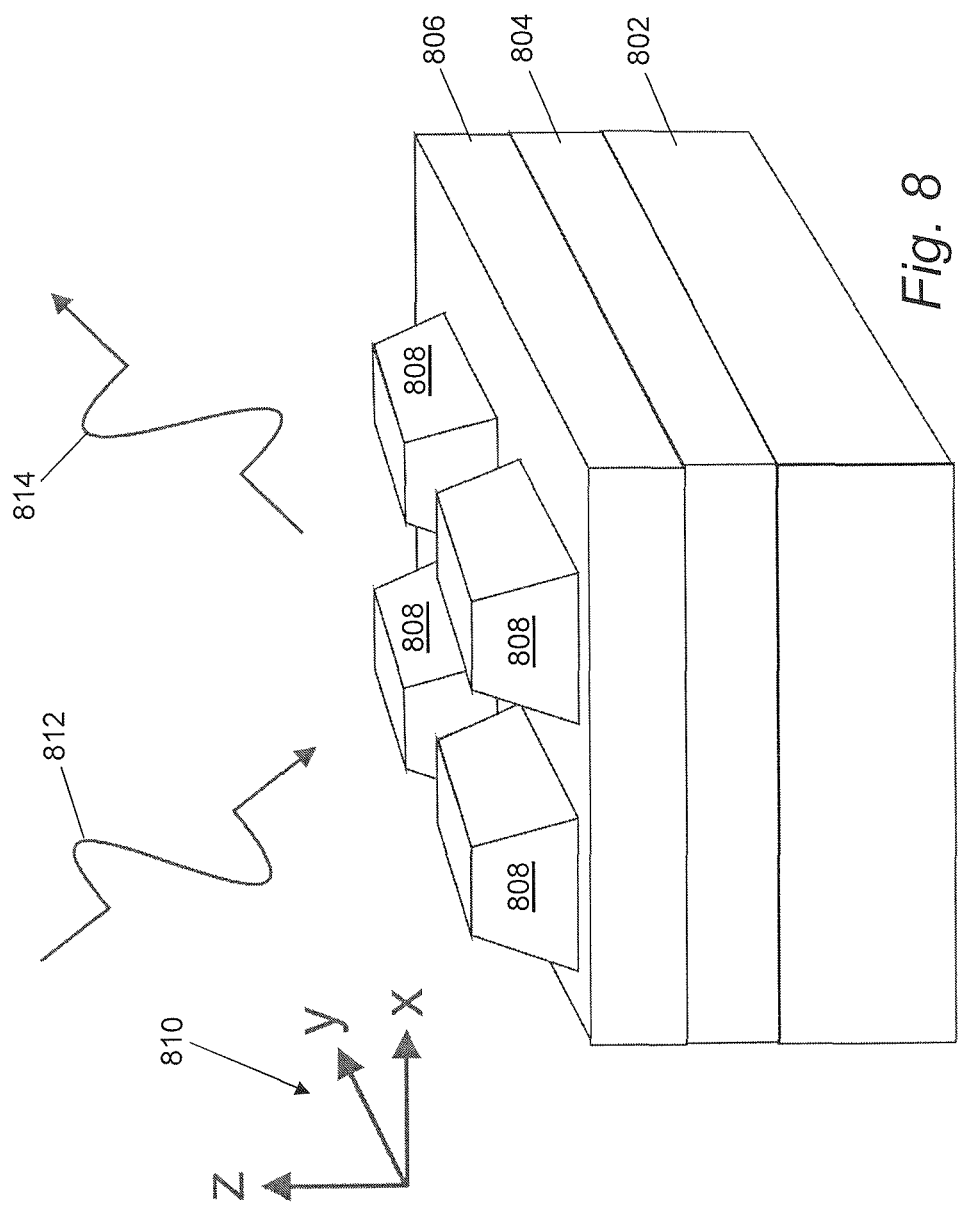
FIG. 8 depicts the scattering geometry that may be reconstructed in accordance with an embodiment of the present invention.

FIG. 8 illustrates schematically the scattering geometry that may be reconstructed in accordance with an embodiment of the present invention. A substrate 802 is the lower part of a medium layered in the z direction. Other layers 804 and 806 are shown. A two dimensional grating 808 that is periodic in x and y is shown on top of the layered medium. The x, y and z axes are also shown 810. An incident field 812 interacts with and is scattered by the structure 802 to 808 resulting in a reflected field 814. Thus the structure is periodic in at least one direction, x, y, and includes materials of differing properties such as to cause a discontinuity in an electromagnetic field, Etot, that comprises a total of incident, Einc, and scattered, Es, electromagnetic field components at a material boundary between the differing materials.

Figure 9:
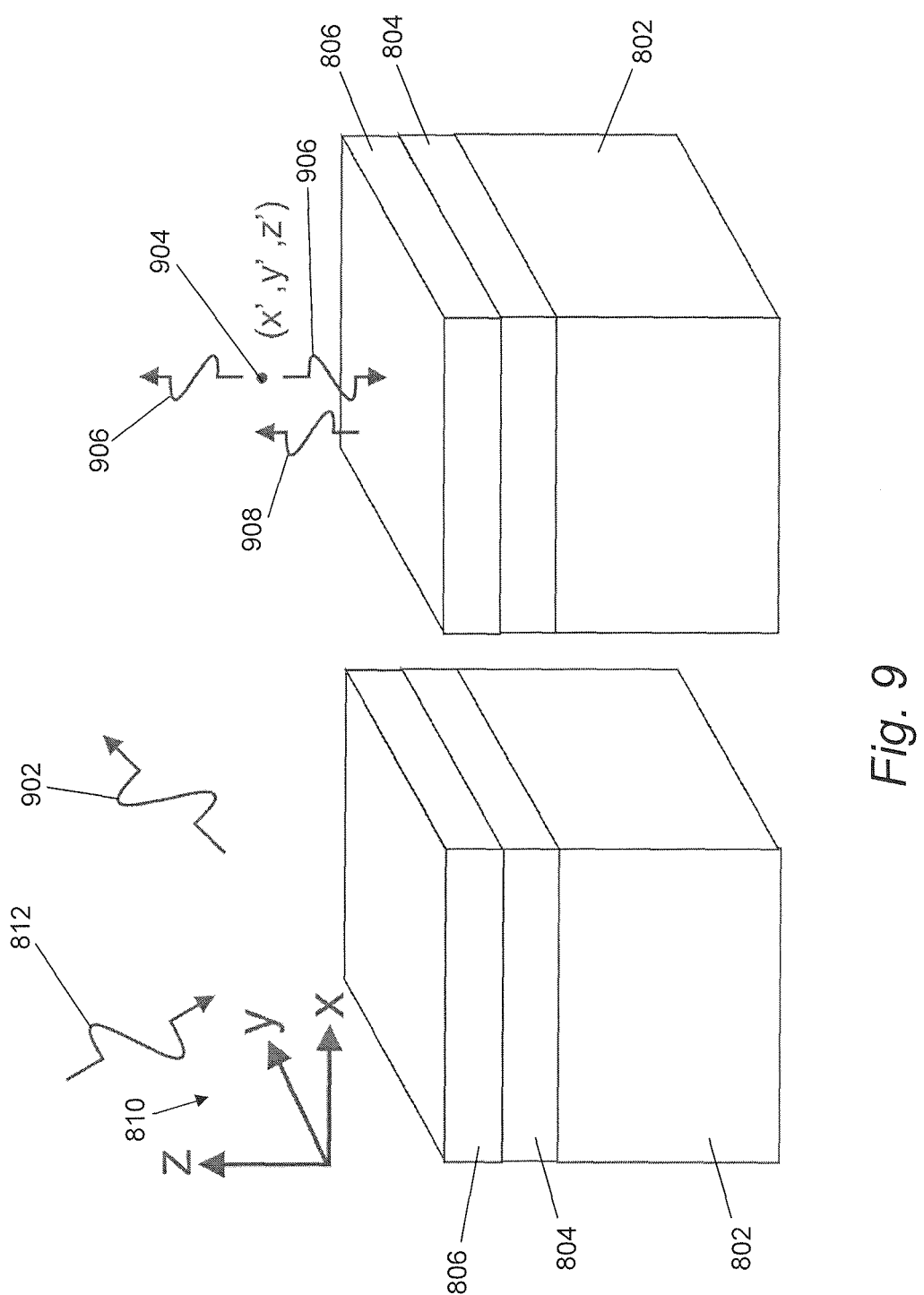
FIG. 9 depicts the structure of the background and illustrates use of a Green's function to calculate the interaction of the incident field with the layered medium.

FIG. 9 shows the structure of the background and schematically illustrates the Green's function that may be used to calculate the interaction of the incident field with the layered medium. The layered medium 802 to 806 is labeled the same as in FIG. 8. The x, y and z axes are also shown 810 along with the incident field 812. A directly reflected field 902 is also shown. The point source (x', y', z') 904 represents the Green's function interaction with the background that generates a field 906. In this case because the point source 904 is above the top layer 806 there is only one background reflection 908 from the top interface of 806 with the surrounding medium. If the point source is within the layered medium then there will be background reflections in both up and down directions (not shown).

The VIM formula to be solved is $$E^{inc}(x,y,z) = E^{tot}(x,y,z) - \iiint \overline{G}(x,x',y,y',z,z') J^c(x',y',z') dx' dy' dz' \quad (0.1)$$

$$J^c(x',y',z') = \chi(x',y',z') E^{tot}(x',y',z') \quad (0.2)$$

In this equation, the incident field $E^{inc}$ is a known function of angle of incidence, polarization and amplitude, $E^{tot}$ is the total electric field that is unknown and for which the solution is calculated, $J^c$ is the contrast current density, $\overline{G}$ is the Green's function (a 3×3 matrix), $\chi$ is the contrast function given by $j\omega(\epsilon(x,y,z,) - \epsilon_b(z))$, where $\epsilon$ is the permittivity of the structure and $\epsilon_b$ is the permittivity of the background medium. $\chi$ is zero outside the gratings.

The Green's function $\overline{G}(x, x', y, y', z, z')$ is known and computable for the layered medium including 802 to 806. The Green's function shows a convolution and/or modal decomposition (m1, m2) in the xy plane and the dominant computation burden along the z axis in $\overline{G}$ are convolutions.

For discretization, the total electric field is expanded in Bloch/Floquet modes in the xy plane. Multiplication with $\chi$ becomes: (a) discrete convolution in the xy plane (2D FFT); and (b) product in z. The Green's function interaction in the xy plane is an interaction per mode. The Green's function interaction in z is a convolution that may be performed with one-dimensional (1D) FFTs with a complexity O(NlogN).

The number of modes in xy is M1M2 and the number of samples in z is N.

The efficient matrix-vector product has a complexity O(M1M2N log(M1M2N)) and the storage complexity is O(M1M2N).

The VIM solution method for Ax=b is performed using an iterative solver based on a Krylov subspace method, e.g., BiCGstab(1) (Stabilized BiConjugate Gradient method), which typically has the steps:

Define residual error as rn=b−Axn

Compute update vector(s) vn via residual error

Update solution: xn+1=xn+αn vn

Update residual error rn+1=rn−αn Avn

Figure 10:
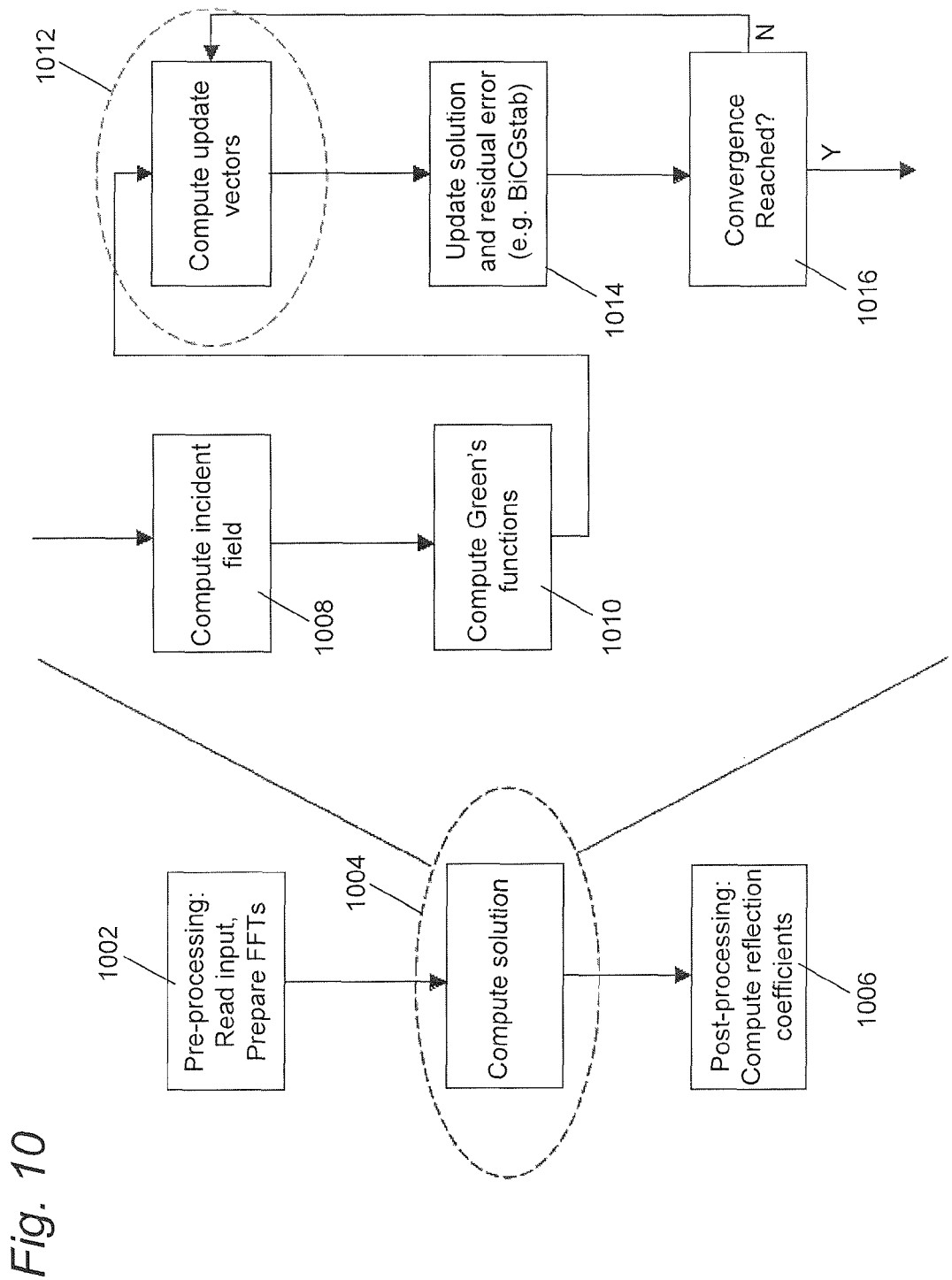
FIG. 10 is a flow chart of the high level method of solving the linear system corresponding to the VIM formula.

FIG. 10 is a flow chart of the high level method of solving the linear system corresponding to the VIM formula. This is a method of calculating electromagnetic scattering properties of a structure, by numerically solving a volume integral. At the highest level the first step is pre-processing 1002, including reading the input and preparing FFTs. The next step is to compute the solution 1004. Finally, post-processing 1006 is performed in which reflection coefficients are computed. Step 1004 includes various steps also shown at the right hand side of FIG. 10. These steps are computing the incident field 1008, computing the Green's Functions 1010, computing the update vectors 1012, updating the solution and residual error (e.g., using BiCGstab) 1014 and testing to see if convergence is reached 1016. If convergence is not reached control loops back to step 1012 that is the computation of the update vectors.

Figure 11:
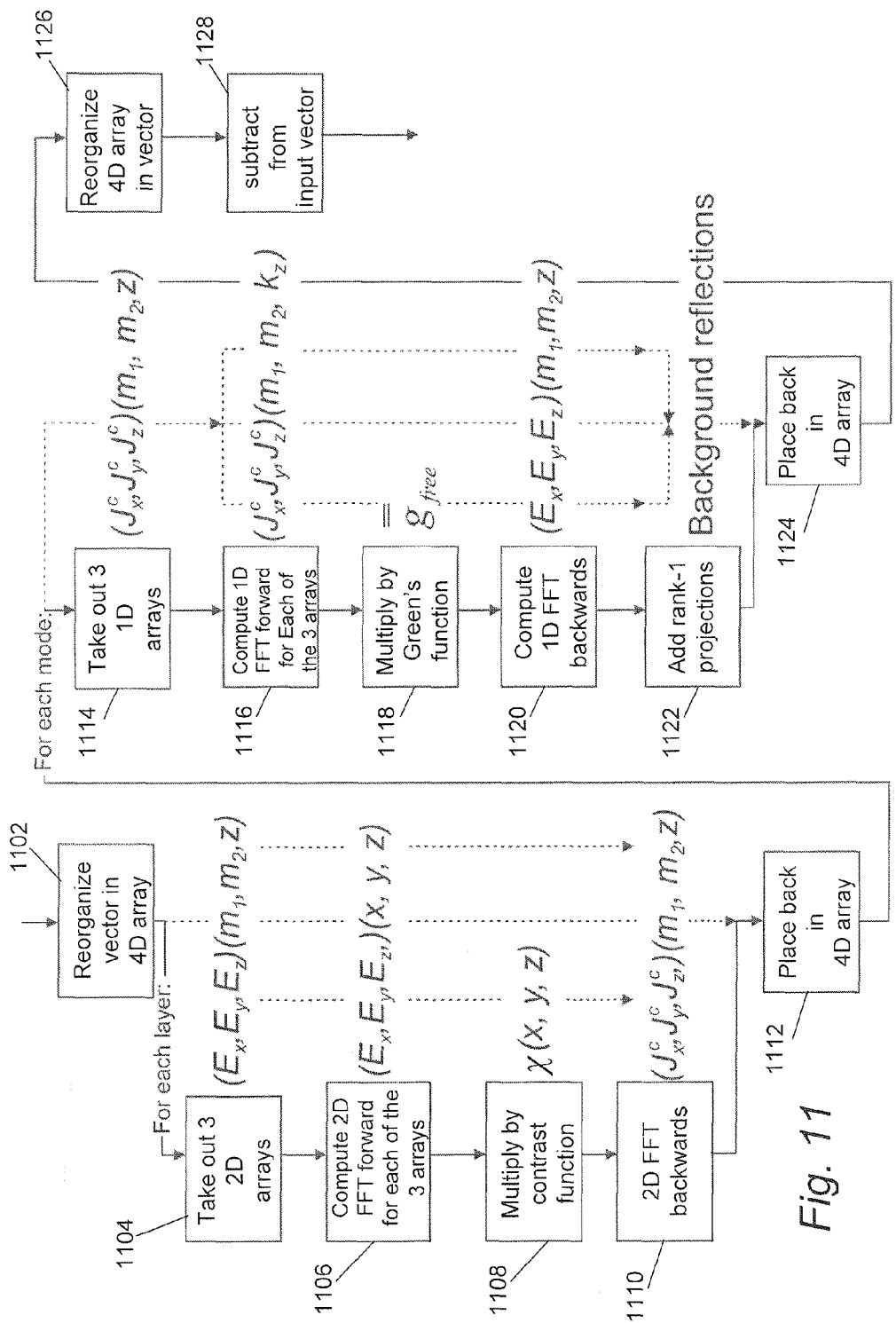
FIG. 11 is a flow chart of the computation of update vectors using the VIM formula as known in the prior art.

FIG. 11 illustrates the steps in computing update vectors corresponding to step 1012 of FIG. 10 using the volume integral method as known in the prior art, which is a method of calculating electromagnetic scattering properties of a structure, by numerically solving a volume integral equation for an electric field, E.

In the spectral domain, the integral representation that describes the total electric field in terms of the incident field and contrast current density, where the latter interacts with the Green's function, viz $$e^i(m_1, m_2, z) = e(m_1, m_2, z) - \int_{-\infty}^{\infty} \overline{G}(m_1, m_2, z, z') j(m_1, m_2, z') dz' \quad (1.1)$$

for $m_1, m_2 \in \mathbb{Z}$. Further, $\overline{G}$ denotes the spectral Green's function of the background medium, which is planarly stratified in the z direction, $e(m_1,m_2,z)$ denotes a spectral component of total electric field E(x,y,z), written in a spectral base in the xy plane, and $j(m_1,m_2,z)$ denotes a spectral component of the contrast current density $J^c(x,y,z)$, also written in a spectral base in the xy plane.

The second equation is a relation between the total electric field and the contrast current density, which is essentially a constitutive relation defined by the materials present in the configuration, viz $$J^c(x,y,z) = j\omega[\epsilon(x,y,z) - \epsilon_b(z)] E(x,y,z) \quad (1.2)$$

where $J^c$ denotes the contrast current density, $\omega$ is the angular frequency, $\epsilon(x,y,z)$ is the permittivity of the configuration, $\epsilon_b(z)$ is the permittivity of the stratified background, and E denotes the total electric field, all written in a spatial basis.

A straightforward approach is to transform Eq. (1.2) directly to the spectral domain, as proposed in [9], i.e.

$$j(m_1, m_2, z) = \sum_{k=M_{1l}}^{M_{1h}} \sum_{\ell=M_{2l}}^{M_{2h}} \chi_s(m_1 - k, m_2 - \ell, z) e(k, \ell, z) \quad (1.3)$$

where $M_{1l}$ and $M_{2l}$ are the spectral lower bounds and $M_{1h}$ and $M_{2h}$ the spectral upper bounds that are taken into account for the finite Fourier representation of E and $J^c$. Further, $\chi_s(k,l,z)$ are the Fourier coefficients of the contrast function $\chi(x,y,z)$ with respect to the transverse (xy) plane.

Step 1102 is reorganizing the vector in a four-dimensional (4D) array. In this array the first dimension has three elements $E_x$, $E_y$ and $E_z$. The second dimension has elements for all values of $m_1$. The third dimension has elements for all values of $m_2$. The fourth dimension has elements for each value of z. Thus the 4D array stores the spectral (in the xy plane) representation of the total electric field $(E_x, E_y, E_z)(m_2, m_2, z)$. The three parallel dotted arrows descending from step 1102 in FIG. 11 correspond to the processing of three 2D arrays, one each for $E_x$, $E_y$ and $E_z$ respectively, by steps 1104 to 1110 carried out for each layer, z. These steps perform the convolution of the spectral (in the xy plane) representation of the electric field $(E_x, E_y, E_z)(m_2, m_2, z)$ with the material properties to calculate the spectral (in the xy plane) representation of the contrast current density $(J_x^c, J_y^c, J_z^c)(m_1, m_2, z)$ corresponding to Equation (1.3). In detail, step 1104 involves taking out the three 2D arrays (the two dimensions being for $m_1$ and $m_2$). In step 1106 a 2D FFT is computed forward for each of the three arrays into the spatial domain. In step 1108 each of the three arrays is multiplied by the spatial representation of the contrast function $\chi(x,y,z)$ that is filtered by the truncation of the Fourier representation. The convolution is completed in step 1110 with the 2D FFT backwards into the spectral (in the xy plane) domain yielding the spectral contrast current density $(J_x^c, J_y^c, J_z^c)(m_1, m_2, z)$. In step 1112 the calculated spectral contrast current density is placed back into the 4D array.

Then for each mode (i.e. for all sample points in z, at the same time), steps 1114 to 1122 are performed. The three dotted parallel arrows descending from beside step 1116 correspond to computing the integral term in Equation (1.1), which is the background interaction with the contrast current density that has itself arisen from the total electric field's interaction with the structure. This is performed by a convolution of $(J_x^c, J_y^c, J_z^c)(m_1, m_2, z)$ with the spatial (with respect to the z direction) Green's function, using a multiplication in the spectral domain (with respect to the z direction).

In detail, in step 1114 the spectral contrast current density $(J_x^c, J_y^c, J_z^c)(m_1, m_2, z)$ is taken out as three 1D arrays for each of x, y, and z. In step 1116, the convolution begins by computing the 1D FFT forward for each of the three arrays into the spectral domain with respect to the z direction to produce $(J_x^c, J_y^c, J_z^c)(m_1, m_2, k_z)$, where kz is the Fourier variable with respect to the z direction. In step 1118 the truncated Fourier transform of the contrast current density is multiplied in the spectral domain (with respect to the z direction) by the Fourier transform of the spatial Green's function $\bar{\bar{g}}_{free}$. In step 1120 a 1D FFT backwards is performed into the spatial domain with respect to the z direction. In step 1122 background reflections (see 908 in FIG. 9) in the spatial domain with respect to z are added. This separation of the background reflections from the Green's function is a conventional technique and the step may be performed by adding rank-1 projections as will be appreciated by one skilled in the art. As each mode is processed then the update vectors for the total electric field, (Ex, Ey, Ez)(m2, m2, z), thus calculated are placed back into the 4D array in step 1124.

The next step is reorganizing the 4D array in a vector 1126, which is different from step 1102 "reorganizing the vector in a 4D array", in that it is the reverse operation: each one-dimensional index is uniquely related to a four-dimensional index. Finally in step 1128 the vector output from step 1126 is subtracted from the input vector, corresponding to the subtraction in the right-hand side of Equation (1.1). The input vector is the vector that enters at step 1102 in FIG. 11 and contains (Ex, Ey, Ez)(m1, m2, z).

A problem with the method described in FIG. 11 is that it leads to poor convergence. This poor convergence is caused by concurrent jumps in permittivity and electric field for the truncated Fourier-space representation. As discussed above, in the VIM method the Li inverse rule is not suitable for overcoming the convergence problem because in VIM the complexity of the inverse rule leads to a very large computational burden because of the very large number of inverse operations that are needed in the VIM numerical solution. Embodiments of the present invention overcome the convergence problems caused by concurrent jumps without resorting to use of the inverse rule as described by Li. By avoiding the inverse rule, embodiments of the present invention do not sacrifice the efficiency of the matrix-vector product that is required for solving the linear system in an iterative manner in the VIM approach.

Figure 12:
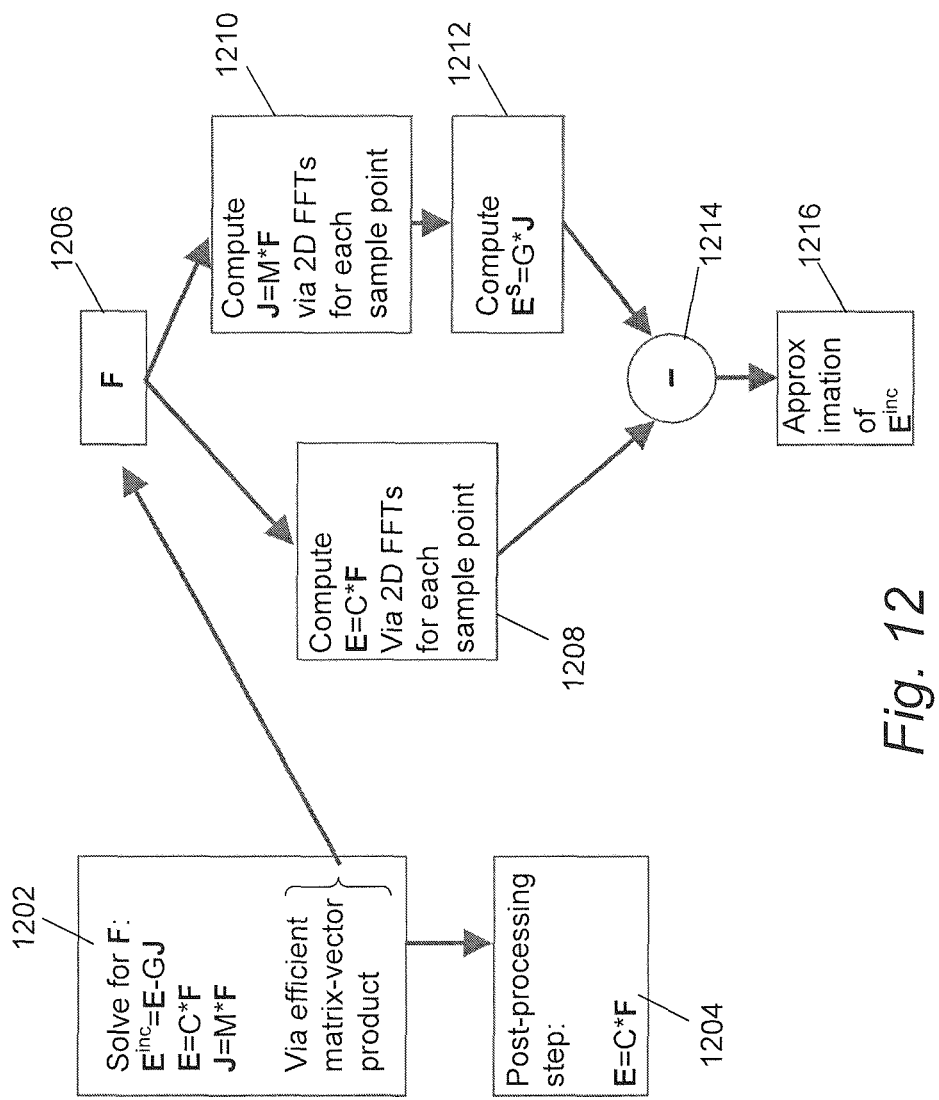
FIG. 12 depicts an embodiment of the present invention using a continuous vector field to numerically solve the VIM formula.

FIG. 12 illustrates an embodiment of the present invention using a continuous vector field to numerically solve the VIM formula. This involves numerically solving a volume integral equation for a vector field, F, that is related to the electric field, E, by a change of basis, the vector field, F, being continuous at one or more material boundaries, so as to determine an approximate solution of the vector field, F. The vector field, F, is represented by at least one finite Fourier series with respect to at least one direction, x, y, and the step of numerically solving the volume integral equation comprises determining a component of the electric field, E, by convolution of the vector field, F, with a convolution-and-change-of-basis operator, C, and determining a current density, J, by convolution of the vector field, F, with a convolution operator, M. The convolution-and-change-of-basis operator, C, is invertible and comprises material and geometric properties of the structure in at least one direction x, y and is configured to transform the vector field, F, to the electric field, E, by performing a change of basis according to the material and geometric properties. The convolution operator, M, comprises material and geometric properties of the structure in the at least one direction, x, y. The current density, J, may be a contrast current density and is represented by at least one finite Fourier series with respect to the at least one direction, x, y. The convolutions are performed using a transformation such as one selected from a set comprising a fast Fourier transform (FFT) and number-theoretic transform (NTT). The convolution-and-change-of-basis operator, C, and the convolution operator, M, operate according to a finite discrete convolution, so as to produce a finite result.

FIG. 12 shows the step 1202 of solving the VIM system for an intermediate vector field, F, with a post-processing step 1204 to obtain a total electric field, E, by convolution of the approximate solution of the vector field, F, with the convolution-and-change-of-basis operator, C. The convolution may be performed using a transformation such as one selected from a set comprising a fast Fourier transform (FFT) and number-theoretic transform (NTT). FIG. 12 also shows at the right hand side a schematic illustration of performing an efficient matrix-vector product 1206 to 1216 to solve the VIM system iteratively. This starts with an intermediate vector field, F, in step 1206. The first time that F is set up, it can be started from zero. After that initial step, the estimates of F are guided by the iterative solver and the residual. Next the total electric field, E, is computed 1208 using the convolution of a convolution-and-change-of-basis operator, C, with the intermediate vector field, F, via 2D FFTs for each sample point in the z direction. The convolution-and-change-of-basis operator, C, is configured to transform the basis of the intermediate vector field, F, to the basis of the total electric field, E. Also, the contrast current density, J, is computed in step 1210 using a convolution of a material convolution operator, M, with the intermediate vector field, F. Step 1210 is performed for each sample point in z with the convolution being performed via 2D FFTs. In step 1212 the convolutions and rank-1 projections between the Green's function, G, and the contrast current density, J, are computed to yield the scattered electric field, Es. The convolution may be performed using a transformation such as one selected from a set comprising a fast Fourier transform (FFT) and number-theoretic transform (NTT). Operation 1214 subtracts the two computed results Es from E to obtain an approximation of Einc 1216. Because steps 1206 to 1216 produce update vectors then the post-processing step 1204 is used to produce the final value of the total electric field, E.

Rather than a separate post-processing step 1204 the sum of all the update vectors may be recorded at step 1208 in order to calculate the total electric field, E. However, that approach increases the storage requirements of the method, whereas the post-processing step 1204 is not costly in storage or processing time, compared to the iterative steps 1206 to 1216.

Figure 13:
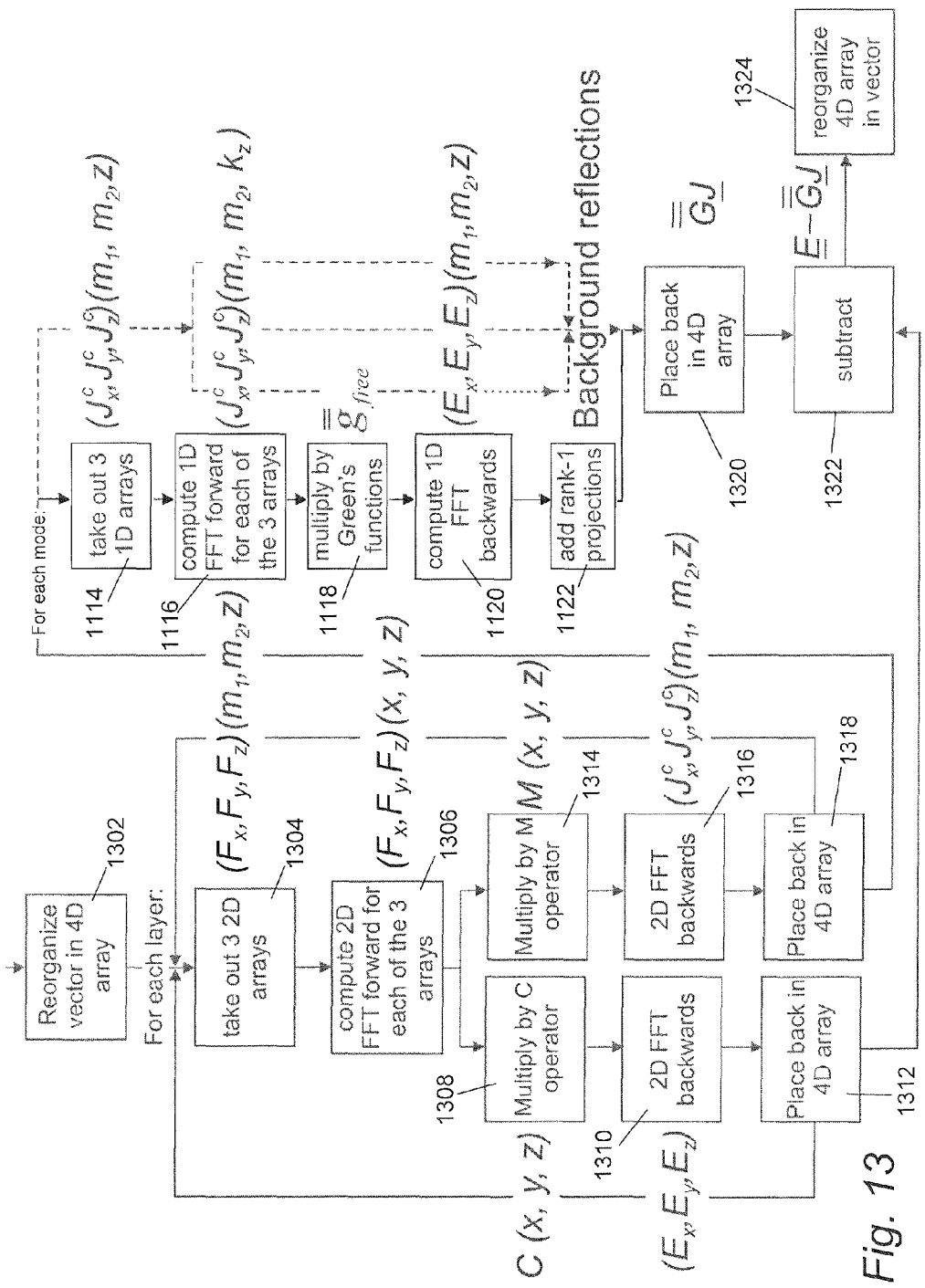
FIG. 13 is a flow chart of the computation of update vectors in accordance with an embodiment of present invention.

FIG. 13 is a flow chart of the computation of update vectors in accordance with an embodiment of present invention. The flow chart of FIG. 13 corresponds to the right hand side (steps 1206 to 1216) of FIG. 12.

In step 1302 the vector is reorganized in a 4D array. Then for each sample point in z, steps 1304 to 1318 are performed. In step 1304 three 2D arrays are taken out of the 4D array. These three 2D arrays $(F_x, F_y, F_z)(m_1, m_2, z)$ correspond to the Cartesian components of the continuous vector field, F, (as described in Equation (3) below), each having the 2 dimensions corresponding to m1 and m2. In 1306 the convolution of the spectral continuous vector field, represented by $(F_x, F_y, F_z)(m_1, m_2, z)$ begins with the computation in step 1306 of the 2D FFT forward into the spatial domain for each of the three arrays, represented by $(F_x, F_y, F_z)(m_1, m_2, z)$. In step 1308 the Fourier transform $(F_x, F_y, F_z)(x, y, z)$ obtained from step 1306 is multiplied in the spatial domain by the spatial multiplication operator $C(x, y, z)$. In step 1310 the product obtained in step 1308 is transformed into the spectral domain by a 2D FFT backwards.

Figure 14:
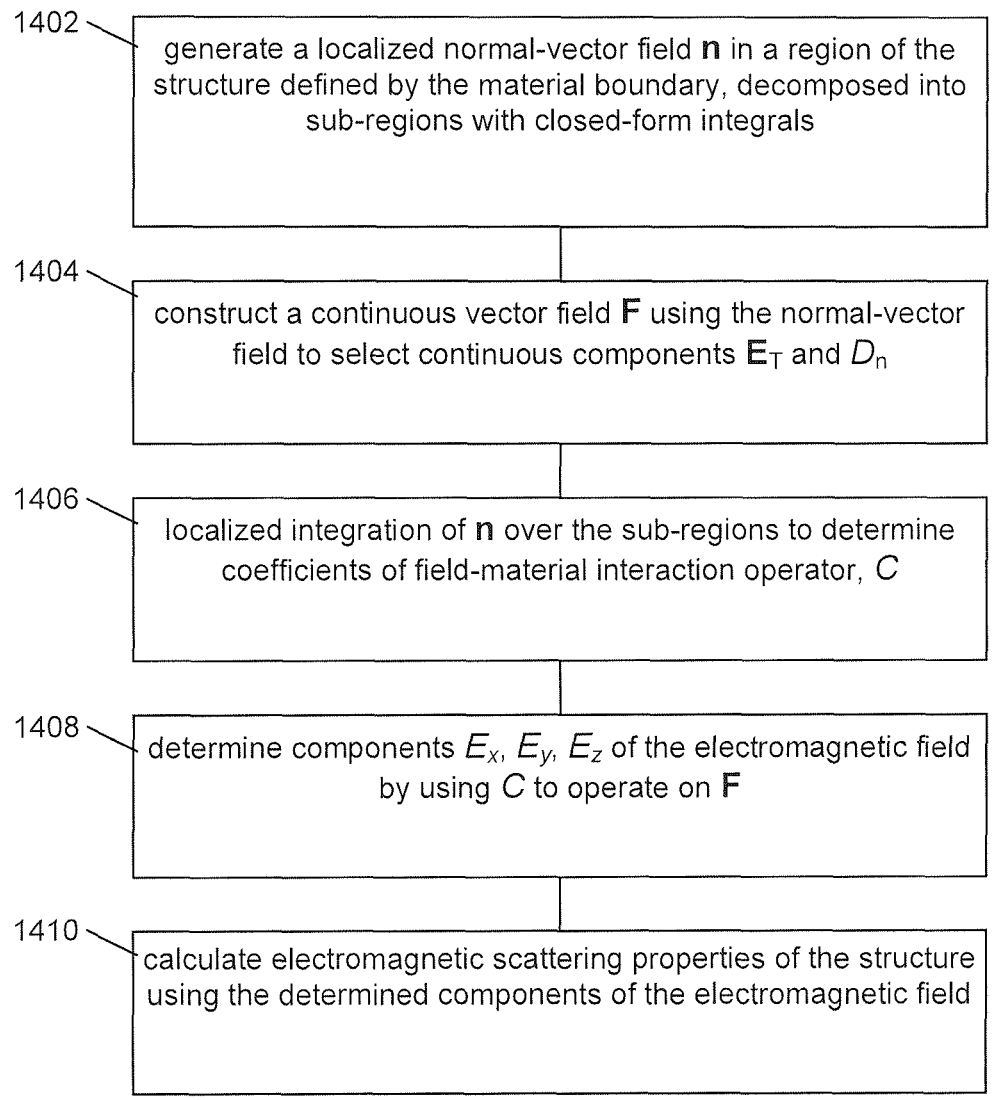
FIG. 14 is a flow chart of a method of calculating electromagnetic scattering properties of a structure in accordance with an embodiment of present invention.

With reference to FIG. 14, the vector field, F, is constructed 1404 from a combination of field components of the electromagnetic field, E, and a corresponding electromagnetic flux density, D, by using a normal-vector field, n, to filter out continuous components of the electromagnetic field, E, tangential to the at least one material boundary, ET, and also to filter out the continuous components of the electromagnetic flux density, D, normal to the at least one material boundary, Dn.

The normal-vector field, n, is generated 1402 in a region of the structure defined with reference to the material boundaries, as described herein. In this embodiment, the region extends to or across the respective boundary. The step of generating the localized normal-vector field may comprise decomposing the region into a plurality of sub-regions, each sub-region being an elementary shape selected to have a respective normal-vector field with possibly a corresponding closed-form integral. These sub-region normal-vector fields are typically predefined. They can alternatively be defined on-the-fly, but that requires additional processing and therefore extra time. The sub-region normal-vector field may be predefined to allow numerical integration by programming a function that gives the (Cartesian) components of the normal-vector field as output, as a function of the position in the sub-region (as input). This function may then be called by a quadrature subroutine to perform the numerical integration. This quadrature rule can be arranged in such a way that all Fourier components are computed with the same sample points (positions in the sub-region), to further reduce computation time. A localized integration of the normal-vector field over the region is performed 1406 to determine coefficients of the field-material interaction operator, which is in this embodiment the convolution-and change-of-basis operator, C (Cε in Equation (4)). In this embodiment, the material convolution operator, M (jω[εCε−εbCε] defined in Equations (4) and (5)), is also constructed using this localized normal-vector field. The step of performing the localized integration may comprise using the respective predefined normal-vector field for integrating over each of the sub-regions.

Components of the electromagnetic field, (Ex, Ey, Ez), are numerically determined 1408 by using the field-material interaction operator, C, to operate on the vector field, F. The electromagnetic scattering properties of the structure, such as reflection coefficients, can therefore be calculated 1410 using the determined components of the electromagnetic field, (Ex, Ey, Ez), in this embodiment by solving a volume integral equation for the vector field, F, so as to determine an approximate solution of the vector field. It should be appreciated that the method is not limited to the Volume Integral Method, and the determined component of the electromagnetic field may be used in other models to calculate electromagnetic scattering properties, such as RCWA or any other solver of Maxwell equations.

The region may correspond to the support of the contrast source.

The step of generating the localized normal-vector field may comprise scaling at least one of the continuous components.

The step of scaling may comprise using a scaling function (α) that is continuous at the material boundary.

The scaling function may be constant. The scaling function may be equal to the inverse of a background permittivity.

The step of scaling may further comprise using a scaling operator (S) that is continuous at the material boundary, to account for anisotropic material properties.

The scaling function may be non-zero. The scaling function may be constant. The scaling function may be equal to the inverse of a background permittivity.

The scaling may be configured to make the continuous components of the electromagnetic field and the continuous components of the electromagnetic flux density indistinguishable outside the region.

The step of generating the localized normal-vector field may comprise using a transformation operator (Tn) directly on the vector field to transform the vector field from a basis dependent on the normal-vector field to a basis independent of the normal-vector field.

The basis independent of the normal-vector field may be the basis of the electromagnetic field and the electromagnetic flux density.

With reference again to FIG. 13, the spectral total electric field, (Ex, Ey, Ez), is then placed back in the 4D array at step 1312. Furthermore, a copy is fed forward to the subtract operation 1322 discussed below.

In step 1314 the Fourier transform $(F_{t1}, F_{t2}, F_n)(x,y,z)$ obtained from step 1306 is multiplied in the spatial domain by the multiplication operator, M. The product of the calculation in step 1314 is transformed in step 1316 by a 2D FFT backwards into the spectral domain to yield the spectral contrast current density, represented by $(J_x^c, J_y^c, J_z^c)(m_1, m_2, z)$. In step 1318 the spectral contrast current density, is placed back in the 4D array.

In order to complete the calculation of the approximation of the known incident electrical field, Einc, the Green's function's interaction with the background is calculated for each mode, m1, m2, by steps 1114 to 1122 in the same manner as described with reference to the corresponding identically numbered steps in FIG. 11.

In step 1320 the resulting convolution of the spectral Green's function of the background, $\overline{G}$, and the spectral contrast current density, J, is placed back in the 4D array. Finally in step 1322 the calculation of the approximation of the known incident electrical field, Einc, is completed with the subtraction of the result of step 1320 from the total electric field fed forward from step 1312 and the final step 1324 reorganizes the 4D array in a vector. The means every four-dimensional index of the 4D array is uniquely related to a one-dimensional index of the vector.

Localized Normal-Vector Field

As mentioned above, the concept of normal-vector fields, as introduced in [1], has been adopted in several computational frameworks, in particular in the differential method (DM) and the rigorously coupled wave analysis (RCWA). The basic idea behind this concept is that normal-vector fields can act as a filter to the components of the electric field E and the electric flux density D. Via this filter, we can extract the continuous components of both E and D, which are complementary, and construct a vector field F that is continuous everywhere, with the possible exception of isolated points and lines that correspond to geometrical edges and corners of the scattering object under investigation. After a general 3D treatment, Section 3 provides a detailed analysis for 2D normal-vector fields (in the (x, y)-plane of the wafer). The latter is compatible with a slicing strategy of a 3D geometry along the wafer normal (z-axis), similar to the slicing strategy adopted in RCWA.

An embodiment of the present invention provides a localized normal-vector field. This enables a cut-and-connect technique with basic building blocks that allows for a rapid and flexible generation of a normal-vector field for more complicated shapes. Embodiments of the present invention address the above issues regarding setup time and continuity under parameter changes mentioned above, by employing parameterized building blocks with normal-vector fields that vary continuously as a function of the parameters, such as varying dimensions of a grating structure during iterative reconstruction.

1. Normal-Vector Field Formulation

A suitable starting point for the discussion is found in the paper [1]. One of the main ideas put forward there, is the introduction of a normal-vector field n(x, y, z) over the entire domain of computation. This normal-vector field satisfies two conditions It is pointing orthogonal to every material interface.

It has unit length at every point in space.

Apart from these, there are no other restrictions to define this vector field, although it is convenient to include other properties, such as some form of continuity. Once the normal-vector field has been constructed, two tangential-vector fields $t_1$ (x, y, z) and $t_2$ (x, y, z) can be generated, such that $\{n, t_1, t_2\}$ forms an orthonormal basis at every point in the computational domain. For example, let $n_x$ and $n_y$ be the x and y components of the normal-vector field, then $t_1$ can be constructed as $$t_1 = -n_y u_x + n_x u_y,\qquad(1)$$

where $u_x$ and $u_y$ denote the unit vectors along the x and y direction, respectively. Finally, the vector field $t_2$ is generated via the cross product between n and $t_1$.

The vector field n can be used to filter out the discontinuous component of the electric flux density that results in the continuous scalar field $D_n=(n, D)$, where $(\cdot,\cdot)$ denotes the scalar product. The tangential-vector fields can be used to extract the continuous components of the electric field as $$E_T = (E, t_1)t_1 + (E, t_2)t_2.\qquad(2)$$

Following [1], we now construct the vector field F as $$F = E_T + D_n n = (E, t_1)t_1 + (E, t_2)t_2 + (n, D)n = F_{t_1} t_1 + F_{t_2} t_2 + F_n n,\qquad(3)$$

which is continuous everywhere, with the possible exception of isolated points or lines that correspond to edges and corners in the geometry of the permittivity function.

The key merit of this vector field F is that its continuity allows for field-material interactions in a spectral base via conventional convolution rules. Therefore, it is of prime importance to establish relations between E and D on the one hand and F on the other, i.e., in the notation of [1], the idea is to establish the relations $$E = C_\epsilon F,\qquad(4)$$

$$D = \epsilon C_\epsilon F.\qquad(5)$$

2. Towards Local Normal-Vector Fields 2.1. Projection Operator Framework

To formalize the procedure of filtering out components of the electric field and the electric flux density, we introduce the operator $P_n$ as $$P_n v = (n, v)n,\qquad(6)$$

where v is an arbitrary 3D vector field. From the properties of the normal-vector field n, we observe that $P_n$ is a projection operator and therefore it is idempotent, i.e. $P_n P_n = P_n$. Similarly, we can introduce the operator $P_T$ as $$P_T v = (v, t_1)t_1 + (v, t_2)t_2,\qquad(7)$$

which is also a projection operator. With these projection operators, the vector field F is constructed as $$F = P_T E + P_n D.\qquad(8)$$

Besides the idempotency property, the projection operators $P_T$ and $P_n$ have some other useful properties. First of all, we have $P_T = I - P_n$, where I is the identity operator. This property shows that the normal-vector field itself is sufficient to generate both the operator $P_n$ and the operator $P_T$, which was already observed from the construction of the tangential-vector fields. Second, the operator $P_T$ is mutually orthogonal to $P_n$, i.e. $P_T P_n = P_n P_T = 0$.

2.2. Introducing a Scaling Function

The first improvement that we introduce to the concept of the normal-vector field formalism [1] is the possibility to scale the components of the vector field F. This scaling can take many forms, but for the sake of simplicity we will discuss the scaling of the normal component of the vector field F, i.e.

$$F = E_T + \alpha D_n n,\qquad(9)$$

where α is a non-zero scaling function, which is continuous across material interfaces. The consequences of this scaling are two-fold. First, it can bring the scale of the components of the vector field F to the same order of magnitude. This will improve the conditioning of the linear systems $C_\epsilon$ and $\epsilon C_\epsilon$. Second, and more importantly, it has far-reaching consequences for the locality of the normal-vector field n, as will be demonstrated below. In fact, the second aspect is so important that it will usually guide the choices for scaling, even if it results in a sub-optimal conditioning.

2.3. Field-Material Interactions

We will now show how these operators $P_n$ and $P_T$ can be used to construct the operators in Eq. (4) from the vector field F. To this end, we start from the spatial-domain relations between the electric field and electric flux density on the one hand and the definition of the vector field F on the other. We have $$D = M_\epsilon E,\qquad(10)$$

$$E = M_\epsilon^{-1} D,\qquad(11)$$

$$F = P_T E + \alpha P_n D,\qquad(12)$$

where $M_\epsilon$ is the spatial multiplication operator that multiplies by the generally anisotropic, permittivity tensor ε and $M_\epsilon^{-1}$ is the multiplication operator that multiplies by the (pointwise) inverse of the permittivity tensor.

First, we establish a relation between E and F. Since we have $$E = P_n E + P_T E, \quad (13)$$

$$P_T F = P_T E, \quad (14)$$

$$\frac{1}{\alpha} P_n F = P_n M_\varepsilon E \quad (15)$$
$$= (P_n M_\varepsilon P_n) E + (P_n M_\varepsilon P_T) E$$
$$= (P_n M_\varepsilon P_n) E + (P_n M_\varepsilon P_T) F.$$

After rearranging the latter equation and employing the idempotency of $P_n$, we obtain $$P_n E = (P_n M_\varepsilon P_n)^{-1} \left( \frac{1}{\alpha} P_n - P_n M_\varepsilon P_T \right) F, \quad (16)$$

where $(P_n M_\varepsilon P_n)^{-1}$ is the inverse of $(P_n M_\varepsilon P_n)$ on the range of $P_n$, i.e. $(P_n M_\varepsilon P_n)^{-1} (P_n M_\varepsilon P_n) = P_n$.

Hence, the linear operator $C_\varepsilon$ in Eq. (4) is given by $$E = C_\varepsilon F = \left[ P_T + (P_n M_\varepsilon P_n)^{-1} \left( \frac{1}{\alpha} P_n - P_n M_\varepsilon P_T \right) \right] F. \quad (17)$$

Further, we employ the relations $P_T = I - P_n$ and $(P_n M_\varepsilon P_n)^{-1} (P_n M_\varepsilon P_n) = P_n$, to arrive at $$C_\varepsilon = I + (P_n M_\varepsilon P_n)^{-1} \left( \frac{1}{\alpha} P_n - P_n M_\varepsilon \right) = I + M_{\tilde\varepsilon} P_n \left( \frac{1}{\alpha} I - M_\varepsilon \right), \quad (18)$$

where we have introduced the notation $M_{\tilde\varepsilon} P_n = P_n M_{\tilde\varepsilon} = (P_n M_\varepsilon P_n)^{-1}$, where $M_{\tilde\varepsilon}$ is a scalar multiplication operator.

In a similar way, we can derive a relation between the electric flux density and the vector field F:

$$D = P_n D + P_T D = \frac{1}{\alpha} P_n F + P_T D, \quad (19)$$

$$P_T D = P_T M_\varepsilon E \quad (20)$$
$$= P_T M_\varepsilon P_T E + P_T M_\varepsilon P_n E$$
$$= P_T M_\varepsilon P_T F + P_T M_\varepsilon P_n E.$$

In the second equation, we can now employ Eq. (16) to eliminate E, i.e.

$$P_T D = P_T M_\varepsilon P_T F + P_T M_\varepsilon (P_n M_\varepsilon P_n)^{-1} \left( \frac{1}{\alpha} P_n - P_n M_\varepsilon P_T \right) F. \quad (21)$$

Hence, $$D = \varepsilon C_\varepsilon F \quad (22)$$
$$= \left[ \frac{1}{\alpha} P_n + P_T M_\varepsilon P_T + P_T M_\varepsilon (P_n M_\varepsilon P_n)^{-1} \left( \frac{1}{\alpha} P_n - P_n M_\varepsilon P_T \right) \right] F$$
$$= \left[ \frac{1}{\alpha} P_n + P_T M_\varepsilon C_\varepsilon \right] F.$$

By again employing the relation $P_T = I - P_n$ and the expression for $C_\varepsilon$ in Eq. (18), we have $$\varepsilon C_\varepsilon = M_\varepsilon C_\varepsilon + P_n \left( \frac{1}{\alpha} I - M_\varepsilon C_\varepsilon \right) \quad (23)$$
$$= M_\varepsilon C_\varepsilon + \left( \frac{1}{\alpha} P_n - P_n M_\varepsilon C_\varepsilon \right)$$
$$= M_\varepsilon C_\varepsilon + \left[ \frac{1}{\alpha} P_n - P_n M_\varepsilon + P_n M_\varepsilon M_{\tilde\varepsilon} P_n \left( \frac{1}{\alpha} I - M_\varepsilon \right) \right].$$

Owing to the property $$P_n M_\varepsilon M_{\tilde\varepsilon} P_n = P_n M_\varepsilon P_n M_{\tilde\varepsilon} = (P_n M_\varepsilon P_n) P_n M_{\tilde\varepsilon} = P_n, \quad (24)$$

we finally end up with $$\varepsilon C_\varepsilon = M_\varepsilon C_\varepsilon + \frac{1}{\alpha} P_n - P_n M_\varepsilon + P_n \left( \frac{1}{\alpha} I - M_\varepsilon \right) = M_\varepsilon C_\varepsilon. \quad (25)$$

In the latter operator representation, it is essential that the operator product $M_\varepsilon C_\varepsilon$ is considered as a single multiplication operator. Otherwise, the rationale behind the Li rules is not maintained since $M_\varepsilon$ and $C_\varepsilon$ have concurring jumps in the spatial domain.

From the representations of $C_\varepsilon$ and $\varepsilon C_\varepsilon$ in Eqs (18) and (25), we observe that the projection operator $P_n$ (including its appearance in $M_{\tilde\varepsilon}$) only occurs in combination with the operator $1/\alpha I - M_\varepsilon$. Hence, in principle, the support of the latter operator determines the domain over which the normal-vector field n is required to generate the coefficients of the operators $C_\varepsilon$ and $\varepsilon C_\varepsilon$.

2.3.5. Boundary-Conforming Anisotropy

In other modeling approaches for electromagnetic scattering, directions of anisotropy of medium parameters are expressed in terms of a global coordinate system, not taking into account the geometry of scattering objects.

One important application in which anisotropic media are used concerns line-edge roughness (LER) or line-width roughness. Although LER can be modeled as 3-dimensional variations along a line, this rigorous modeling approach is usually very time consuming. Therefore, LER is typically modeled via an effective medium approximation, in which a transition layer captures the part of the line that contains the roughness. This transition layer is best modeled as an anisotropic medium. The directions of anisotropy generally depend on the geometrical features of the roughness, see e.g. [12]. Since a line is automatically aligned with the Cartesian coordinate system, boundary-conforming anisotropy is automatically equal to anisotropy along the coordinate axes.

In other approaches, anisotropy is defined independent of the scattering geometry. Regarding edge roughness, anisotropic effective-medium models are known for lines but not for other geometrical shapes, e.g. contact holes with a circular or elliptical cross section.

Embodiments of the present invention employ normal-vector fields to arrive at better numerical convergence. Embodiments may have the ability to model bi-refringent media with respect to the horizontal and vertical directions. It is possible to handle more general anisotropic media in which the directions of anisotropy are pointing along the boundary and normal to the boundary of a pattern, i.e. the anisotropy is boundary-conforming. Following the line of reasoning for a LER effective-medium approach [12], such types of anisotropy provide a natural extension to effective-medium approaches, which are e.g. used to model LER. Moreover, no additional processing is required, since the normal of each boundary is already determined within the normal-vector field approach used as described herein.

We define the vector field F as per equation (12):

$$F = P_T E + \alpha P_n D \tag{25.1}$$

and we have the relation between the flux density and the field strength as $$D = M_\epsilon E \tag{25.2}$$

Further, we define the boundary-conforming anisotropy for the permittivity as $$M_\epsilon = \epsilon_n P_n + \epsilon_T P_T, \tag{25.3}$$

which can be interpreted as a permittivity along the normal direction of a geometry and a different permittivity along the tangential directions of that same geometry.

The flux density D and the field strength E on the one hand, can be related to the auxiliary field F on the other. We obtain $$E = \left[ I + \left( \frac{1}{\alpha \varepsilon_n} - 1 \right) P_n \right] F \tag{25.4}$$

and $$D = \varepsilon_T \left[ I + \left( \frac{1}{\alpha \varepsilon_T} - 1 \right) P_n \right] F \tag{25.5}$$

These formulas maintain the freedom to define normal-vector fields locally and have only small changes in the multiplying factors for the permittivity, as discussed herein.

For binary gratings or staircase-approximated cases in the vertical direction, the boundary-conforming anisotropy can be further extended by splitting the $P_T$ operator into a vertical and a horizontal part, i.e. $P_T = P_z + P_{T1}$, where the latter two operators are mutually orthogonal. The permittivity can then have even three directions of boundary-conforming anisotropy, given by $$M_\epsilon = \epsilon_n P_n + \epsilon_T P_{T1} + \epsilon_z P_z \tag{25.6}$$

The formula to express E in terms of F remains identical to equation (25.4) above. The expression for D becomes $$D = \left[ \frac{1}{\alpha} P_n + \varepsilon_T P_{T1} + \varepsilon_z P_z \right] F \tag{25.7}$$

Assuming that this type of anisotropy is only localized to a layer along the boundary, the normal-vector field remains local and the operators PT1 and Pz are already available.

Thus the electromagnetic flux density is related to the electric field using, in the region in which the localized normal vector field is generated and local to the material boundary, a component of permittivity ∈n normal to the material boundary and at least one other, different, component ∈t, ∈z of permittivity tangential to the material boundary This embodiment widens the range of effective-medium approaches, e.g. for edge roughness on curved boundaries. Moreover, no extra processing is required to set up this model since all ingredients are available. Hence no extra time is spent in setting up the corresponding mathematical and numerical problem.

Since boundary-conforming anisotropy is a suitable way of dealing with edge roughness, it leads to significant speed-up of a CD reconstruction process involving edge roughness.

2.4. Choice of the Vector-Field Basis

Above, we have observed that the normal-vector field has the potential to be localized by choosing a proper scaling between the components of the vector field F. However, for typical Maxwell solvers, the tangential-vector fields and normal-vector field are not representative for the components of the solver. In many cases a Cartesian basis is more suitable, e.g., within VIM, RCWA, or the Differential Method. Since a projection operator does not change the basis of the vector field, an additional transformation of the electric field and the electric flux density may be required, to arrive at the required basis for the Maxwell solver. A similar remark holds for the permittivity operator $M_\epsilon$, which is typically expressed in terms of Cartesian coordinates. Therefore, if the basis is different, the operator $M_\epsilon$ must be transformed too. We note that the operator $M_\xi$ also contains the operator $M_\epsilon$. However, since $M_\xi$ is a scalar multiplication, its final form is independent of the chosen basis. Further, the definition of the projection operator $P_n$ as given in Eq. (6) is independent of the chosen basis, although its actual matrix representation does depend on the chosen basis for the normal vector field. Therefore, we choose to write $P_n$ as a basis-independent operator.

Let us now introduce a transformation operator $T_n$, which transforms a vector field expressed in terms of the normal and tangential basis into e.g., Cartesian vector fields that are used for the electric field, the electric flux density, and the permittivity operator $M_\epsilon$. Then we can write for the electric field, expressed in Cartesian coordinates $$\begin{aligned} E &= T_n C_\varepsilon F \\ &= T_n \left[ I + M_\xi P_n \left( \frac{1}{\alpha} I - T_n^{-1} M_\varepsilon T_n \right) \right] F \\ &= \left[ T_n + T_n M_\xi P_n \left( \frac{1}{\alpha} I - T_n^{-1} M_\varepsilon T_n \right) \right] F, \end{aligned} \tag{26}$$

where we have assumed that F is written in the normal and tangential basis.

The immediate consequence is that the normal-vector field and the tangential-vector fields are required on the entire computational domain, due to the presence of the identity operator in $C_\varepsilon$. However, we can also rearrange the above formula, owing to the fact that $M_\epsilon$ also contains the same basis transformation, as $$\begin{aligned} E &= T_n C_\varepsilon F \\ &= \left[ T_n + T_n M_\xi P_n \left( \frac{1}{\alpha} I - T_n^{-1} M_\varepsilon T_n \right) \right] F \\ &= \left[ T_n + T_n M_\xi P_n T_n^{-1} \left( \frac{1}{\alpha} I - M_\varepsilon \right) T_n \right] F \\ &= \tilde{C}_\varepsilon T_n F \\ &= \tilde{C}_\varepsilon (T_n F), \end{aligned} \tag{27}$$

where we have introduced the operator $$\tilde{C}_\varepsilon = I + T_n M_\xi P_n T_n^{-1}\left(\frac{1}{\alpha}I - M_\varepsilon\right).$$

This indicates that the transformation operator can act directly on F, which has again the potential to lead to localized normal-vector field, as long as we consider $T_n F$ as the unknown, i.e. we directly write F in the basis of E and D. A similar derivation for $\epsilon C_\epsilon$ shows $$D = T_n \epsilon C_\epsilon F = T_n(T_n^{-1} M_\epsilon T_n)$$
$$C_\epsilon F = M_\epsilon T_n C_\epsilon F = M_\epsilon \tilde{C}_\epsilon T_n F = \epsilon \tilde{C}_\epsilon (T_n F), \quad (28)$$

owing to the relation $T_n C_\epsilon = \tilde{C}_\epsilon T_n$ as shown above.

2.5. Isotropic Media

A very important class to consider are isotropic media. For such media, the multiplication operator $M_\epsilon$ is a scalar multiplier that acts on each component of the field equally. Therefore, the transformation $T_n$ has no impact on $M_\epsilon$. Further, the formulas for $C_\epsilon$ and $\epsilon C_\epsilon$ are significantly simplified. For the isotropic case, we now consider the consequences of expressing F in Cartesian coordinates, as well as E and D. For this situation we have $$E = \tilde{C}_\epsilon F = I + T_n P_n T_n^{-1}(M_{1/\alpha\epsilon} - I)F, \quad (29)$$

$$D = \epsilon \tilde{C}_\epsilon F = M_\epsilon + T_n P_n T_n^{-1} M_\epsilon (M_{1/\alpha\epsilon} - I)F, \quad (30)$$

where we have introduced the multiplication operator $M_{1/\alpha\epsilon}$ as the point-wise multiplication by the (scalar) function $1/(\alpha\epsilon)$, which results in a scalar multiplication of the identity operator. Hence, $$M_{\frac{1}{\alpha\varepsilon}} - I = \left(\frac{1}{\alpha\varepsilon} - 1\right)I. \quad (31)$$

There are now a number of choices for α:

Choose α to be a constant equal to $1/\epsilon_b$, i.e. the inverse of the (local) background permittivity. This leads to the consequence that the normal-vector field is only required in regions where the permittivity is different from the background permittivity, i.e. in the regions where the contrast function is non-zero. This choice is particularly interesting if there are only two media present in the grating structure, one of which is the background material.

A second choice is also to choose α as being constant. However, depending on the grating structure, it may be more advantageous to choose a different constant. An important case is a grating where the permittivity of the background occurs in a domain that does not cross the boundaries of the unit cell. This is for instance the case for a circular contact hole in resist, where the filling material of the contact hole is chosen as the background medium. This choice then leads to simpler formulas for the normal-vector field on a circle, as opposed to a normal-vector field for a unit cell with a circle left out, for which it is much harder to compute the resulting integrals.

A third choice is to let α be a continuous function, such that it is a smoothed version of the original inverse permittivity function, e.g., via tri-linear interpolation or averaging by a Gaussian window. In that case, the normal-vector field is only required in the direct vicinity of the interface between materials and it becomes even more localized. However, the resulting integrals that have to be computed are typically more difficult. By selecting where to start the transition to gradually change from one permittivity to the other, it is possible to end up with localized normal-vector fields that are needed on only one side of the interface between two media.

In general, it is more complicated to go outside the boundary if other close structures are present, since that will make the cut-and-connect strategy, as will be discussed later on, much more complicated.

2.6. Expressions for the Field-Material Interaction Coefficients for Isotropic Media Let us now take a closer look at the field-material interaction operators $\tilde{C}_\epsilon$ and $\epsilon\tilde{C}_\epsilon$. We assume that the electric field, the electric flux density, the vector field F, and the normal-vector field n are written in terms of their Cartesian components. Then, we have the following spatial relations, obtained from Eq. (29), $$\begin{pmatrix} E_x \\ E_y \\ E_z \end{pmatrix} = \begin{pmatrix} C_{xx} & C_{xy} & C_{xz} \\ C_{yx} & C_{yy} & C_{yz} \\ C_{zx} & C_{zy} & C_{zz} \end{pmatrix} \begin{pmatrix} F_x \\ F_y \\ F_z \end{pmatrix}, \quad (32)$$

where $$C_{xx} = 1 + n_x^2(x,y,z)\left[\frac{1}{\alpha(x,y,z)\varepsilon(x,y,z)} - 1\right], \quad (33)$$

$$C_{xy} = n_x(x,y,z)n_y(x,y,z)\left[\frac{1}{\alpha(x,y,z)\varepsilon(x,y,z)} - 1\right], \quad (34)$$

$$C_{xz} = n_x(x,y,z)n_z(x,y,z)\left[\frac{1}{\alpha(x,y,z)\varepsilon(x,y,z)} - 1\right], \quad (35)$$

$$C_{yx} = n_x(x,y,z)n_y(x,y,z)\left[\frac{1}{\alpha(x,y,z)\varepsilon(x,y,z)} - 1\right], \quad (36)$$

$$C_{yy} = 1 + n_y^2(x,y,z)\left[\frac{1}{\alpha(x,y,z)\varepsilon(x,y,z)} - 1\right], \quad (37)$$

$$C_{yz} = n_y(x,y,z)n_z(x,y,z)\left[\frac{1}{\alpha(x,y,z)\varepsilon(x,y,z)} - 1\right], \quad (38)$$

$$C_{zx} = n_x(x,y,z)n_z(x,y,z)\left[\frac{1}{\alpha(x,y,z)\varepsilon(x,y,z)} - 1\right], \quad (39)$$

$$C_{zy} = n_y(x,y,z)n_z(x,y,z)\left[\frac{1}{\alpha(x,y,z)\varepsilon(x,y,z)} - 1\right], \quad (40)$$

$$C_{zz} = 1 + n_z^2(x,y,z)\left[\frac{1}{\alpha(x,y,z)\varepsilon(x,y,z)} - 1\right], \quad (41)$$

and $$\begin{pmatrix} D_x \\ D_y \\ D_z \end{pmatrix} = \begin{pmatrix} \varepsilon C_{xx} & \varepsilon C_{xy} & \varepsilon C_{xz} \\ \varepsilon C_{yx} & \varepsilon C_{yy} & \varepsilon C_{yz} \\ \varepsilon C_{zx} & \varepsilon C_{zy} & \varepsilon C_{zz} \end{pmatrix} \begin{pmatrix} F_x \\ F_y \\ F_z \end{pmatrix} \quad (42)$$

where $$\varepsilon C_{xx} = \varepsilon(x,y,z) + n_x^2(x,y,z)\left[\frac{1}{\alpha(x,y,z)} - \varepsilon(x,y,z)\right], \quad (43)$$

$$\varepsilon C_{xy} = n_x(x,y,z)n_y(x,y,z)\left[\frac{1}{\alpha(x,y,z)} - \varepsilon(x,y,z)\right], \quad (44)$$

$$\varepsilon C_{xz} = n_x(x,y,z)n_z(x,y,z)\left[\frac{1}{\alpha(x,y,z)} - \varepsilon(x,y,z)\right], \quad (45)$$

$$\varepsilon C_{xx} = n_x(x,y,z)n_y(x,y,z)\left[\frac{1}{\alpha(x,y,z)} - \varepsilon(x,y,z)\right], \quad (46)$$

-continued $$\varepsilon C_{yy} = \varepsilon(x, y, z)n_y^2(x, y, z)\left[\frac{1}{\alpha(x, y, z)} - \varepsilon(x, y, z)\right], \quad (47)$$

$$\varepsilon C_{yz} = n_y(x, y, z)n_z(x, y, z)\left[\frac{1}{\alpha(x, y, z)} - \varepsilon(x, y, z)\right], \quad (48)$$

$$\varepsilon C_{zx} = n_x(x, y, z)n_z(x, y, z)\left[\frac{1}{\alpha(x, y, z)} - \varepsilon(x, y, z)\right], \quad (49)$$

$$\varepsilon C_{yz} = n_y(x, y, z)n_z(x, y, z)\left[\frac{1}{\alpha(x, y, z)} - \varepsilon(x, y, z)\right], \quad (50)$$

$$\varepsilon C_{zz} = \varepsilon(x, y, z)n_z^2(x, y, z)\left[\frac{1}{\alpha(x, y, z)} - \varepsilon(x, y, z)\right], \quad (51)$$

Since all components of the electric field E, the electric flux density D, and the auxiliary vector field F are expressed in a spectral basis with respect to the x and y direction, e.g., $$\begin{pmatrix} E_x(x, y, z) \\ E_y(x, y, z) \\ E_z(x, y, z) \end{pmatrix} = \sum_{m_1=M_{1l}}^{M_{1h}} \sum_{m_2=M_{2l}}^{M_{2h}} \begin{pmatrix} e_x(m_1, m_2, z) \\ e_y(m_1, m_2, z) \\ e_z(m_1, m_2, z) \end{pmatrix} \quad (52)$$

$$\exp\{-j[(k_x^{m_1, m_2} + k_x^i)x + (k_y^{m_1, m_2} + k_y^i)y]\},$$

where $k_x^{m_1,m_2}$ and $k_y^{m_1,m_2}$ depend on the directions of periodicity and $k_x^i$ and $k_y^i$ depend on the angle of incidence of the incident field. In this spectral base, the field-material interactions above become convolutions in the xy plane. For example, for i, j∈{x, y, z} we have $$Q_i(x, y, z) = C_{ij}(x, y, z)F_j(x, y, z) \leftrightarrow q_i(m_1, m_2, z) \quad (53)$$

$$= \sum_{l_1=M_{1l}}^{M_{1h}} \sum_{l_2=M_{2l}}^{M_{2h}} c_{ij}(m_1 - l_1, m_2 - l_2, z)f_j(l_1, l_2, z),$$

where $$c_{ij}(m_1, m_2, z) = \frac{1}{\|S\|} \iint_S C_{ij}(x, y, z)\exp[j(k_x^{m_1,m_2}x + k_y^{m_1,m_2}y)]dxdy, \quad (54)$$

where S denotes the unit cell in the xy plane and $\|S\|$ denotes its area. This means that we have to compute the Fourier integrals in the xy plane of the coefficients $C_{ij}$ and $\epsilon C_{ij}$ for i, j∈{x, y, z}. For certain combinations of normal-vector fields and scattering geometries, this can be performed in closed form, e.g., for circles and rectangles as shown in Section 3. For more general shapes, these coefficients can either be approximated by a meshing strategy (Section 4) or by numerical quadrature (Section 5).

2.7. Bi-Refringence in Binary and Staircase Gratings

A second important class of problems is the case in which the grating material(s) have birefringent material properties, where the axis of anisotropy is the z-axis, i.e.

$$\varepsilon = \begin{pmatrix} \varepsilon_{xx} & \varepsilon_{xy} & \varepsilon_{xz} \\ \varepsilon_{yx} & \varepsilon_{yy} & \varepsilon_{yz} \\ \varepsilon_{zx} & \varepsilon_{zy} & \varepsilon_{zz} \end{pmatrix} = \begin{pmatrix} \varepsilon_T & 0 & 0 \\ 0 & \varepsilon_T & 0 \\ 0 & 0 & \varepsilon_N \end{pmatrix}, \quad (55)$$

where $\epsilon_T$ and $\epsilon_N$ are, in principle, functions of x, y, and z.

We now consider the case of a binary grating, which has invariant cross section along the z-axis over the interval z∈[$z_l$, $z_h$], as well as permittivity profile independent of z. For such a binary grating, we choose one of the tangential-vector fields to be aligned along the z-axis, i.e. $t_2 = u_z$. This means that n and $t_1$ are two-dimensional vector fields, i.e. their z components are zero. With this choice, the normal-vector field problem in the xy plane is again an isotropic problem and the considerations for the scaling parameter α are now quite similar to those in Section 2.5, e.g., for a two-media problem one should scale the electric flux density with respect to $\epsilon_T$ of the interior or exterior of the object, such that the scaled electric flux density becomes identical to the electric field in a dedicated part of the unit cell.

For more general grating geometries, one can apply a staircase approximation of the grating, with respect to the z direction. Then, the grating consists of a sequence of binary gratings and for each of these binary gratings the strategy outlined above can be followed.

3. Localized Normal-Vector Fields for Binary Gratings with Elliptical and Rectangular Cross Sections In this section, we shall derive the spectral representation of $C_\epsilon$ and $\epsilon C_\epsilon$ for two elementary 2-dimensional shapes: the rectangle and the ellipse. These shapes are often encountered as an integral or elementary building block in 2D wafer metrology structures. This derivation will show the construction of a normal-vector field (NV) and the subsequent computation of the Fourier integral of the matrix elements of $C_\epsilon$ and $\epsilon C_\epsilon$. For a given contour, there is not a unique normal-vector field. Infinitely many NV fields can be constructed that have unit length and are perpendicular to the contour. We shall see that an important motivation for a particular choice is the possibility to derive an analytical expression for the Fourier coefficients of $C_\epsilon$ and $\epsilon C_\epsilon$. Also the number of singularities in the NV field should be minimized to optimize convergence of the Fourier series. The ellipse and the rectangle are so fortunate to have analytical expressions for the Fourier integral.

3.1. Fourier Integral for an Arbitrary Unit Cell

In two dimensions, the periodicity of a lattice is described by its Bravais lattice vectors ($a_1$, $a_2$). A shift over $$R = n_1 a_1 + n_2 a_2, \quad (56)$$

leads to an equivalent lattice position. A plane wave with the same periodicity as the Bravais lattice will have a wave vector K answering the condition $$e^{ik \cdot (r+R)} = e^{iK \cdot r} \Rightarrow e^{iK \cdot R} = 1. \quad (57)$$

The space of all wave vectors that fulfill this condition is called the reciprocal lattice. This space is spanned by two primitive vectors $$b_1 = \frac{2\pi}{(a_{1x}a_{2y} - a_{1y}a_{2x})}\begin{pmatrix} a_{2y} \\ -a_{2x} \\ 0 \end{pmatrix}, \quad (58)$$

$$b_2 = \frac{2\pi}{(a_{1x}a_{2y} - a_{1y}a_{2x})}\begin{pmatrix} -a_{1y} \\ a_{1x} \\ 0 \end{pmatrix}, \quad (59)$$

that answer the orthogonality condition $$b_i \cdot a_j = 2\pi \delta_{ij}, \quad (60)$$

from which Eq. (2) can be proven. The Fourier integral in an arbitrary 2-dimensional lattice is now defined with respect to the basis of plane waves with wave vectors in the reciprocal lattice.

$$F(x, y) = \sum_{m_1,m_2=-\infty}^{\infty} f_{m_1,m_2} e^{-i(m_1 b_1 + m_2 b_2) \cdot r}, \quad (61)$$

where the Fourier coefficient is obtained from the integral $$f_{m_1,m_2} = \iint_{unitcell} F(r) e^{i2\pi(m_1 b_1 + m_2 b_2) \cdot r} d\eta_1 d\eta_2, \quad (62)$$

where $0 \leq \eta_i = a_i/|a_i| \leq 1$ is a dimensionless number spanning each Bravais lattice vector. Transforming to a Cartesian coordinate system gives $$f_{m_1 m_2} = \frac{1}{(a_{1x} a_{2y} - a_{1y} a_{2x})} \iint_{unitcell} F(r) e^{i2\pi(m_1 b_1 + m_2 b_2) \cdot r} dx dy, \quad (63)$$

The 2-dimensional integral in Eq. (54) can now be written as $$c_{ij}(m_1, m_2, z) = \quad (64)$$

$$\frac{1}{(a_{1x}a_{2y} - a_{1y}a_{2x})} \iint_{unitcell} C_{ij}(x, y, z) e^{i[b_{ex}(m_1,m_2)x + b_{ey}(m_1,m_2)y]} dx dy,$$

where $$b_e = \begin{pmatrix} m_1 b_{1x} + m_2 b_{2x} \\ m_1 b_{1y} + m_2 b_{2y} \end{pmatrix}, \quad (65)$$

is the reciprocal lattice vector projected on the Cartesian axes.

Referring to the expressions for $C_{ij}$, Eqs (33)-(41), we see that the diagonal elements contain the Fourier integral of unity over the unit cell and the Fourier integral of the product of normal-vector components and a position-dependent function of the scaling factor $\alpha(x, y, z)$ and the permittivity $\epsilon(x, y, z)$. The first integral, i.e. the integral of unity over the unit cell, is equal to $\delta_{m_1,0}\delta_{m_2,0}$. The second integral can be substantially simplified for the case of an isotropic medium when the scaling factor $\alpha$ is chosen equal to $1/\epsilon_b$. This function is then zero outside and constant inside the support of the contrast source. The Fourier coefficients $c_{ij}(m_1, m_2, z)$ can now be expressed in terms of the integral $$\Gamma_{ij}(m_1, m_2, z) = \frac{1}{(a_{1x}a_{2y} - a_{1y}a_{2x})} \iint_{support} \quad (66)$$

$$n_i(x, y, z) n_j(x, y, z) e^{i[b_{ex}(m_1,m_2)x + b_{ey}(m_1,m_2)y]} dx dy.$$

This simplifies the spectral representation of $C_{ij}$ (Eqs (33)-(41)) to $$c_{ij}(m_1, m_2, z) = \delta_{ij} \delta_{m_1,0} \delta_{m_2,0} + \left(\frac{\varepsilon_b}{\varepsilon_r} - 1\right) \Gamma_{ij}(m_1, m_2, z), \quad (67)$$

and the spectral representation of $\epsilon C_\epsilon$ (Eqs (43)-(51)) to $$[\epsilon C_{xx}] = \epsilon_b \delta_{m_1,0} \delta_{m_2,0} + (\epsilon_r - \epsilon_b) \Gamma_{yy}, \quad (68)$$

$$[\epsilon C_{xy}] = [\epsilon C_{yx}] = (\epsilon_b - \epsilon_r) \Gamma_{xy}, \quad (69)$$

$$[\epsilon C_{yy}] = \epsilon_b \delta_{m_1,0} \delta_{m_2,0} + (\epsilon_r - \epsilon_b) \Gamma_{xx}. \quad (70)$$

In the following sections, closed expressions will be derived for the $\Gamma_{ij}$ integral (Eq. (66)) for the case of the ellipse and the rectangle, but first the integral will be further simplified for translation and rotation of the scattering object.

3.2. Translation and Rotation of the Scattering Object

For the case of elementary shapes like ellipses and rectangles, the computation of the $\Gamma_{ij}$ integral can be further simplified by transforming to the local coordinate system.

Figure 15A:
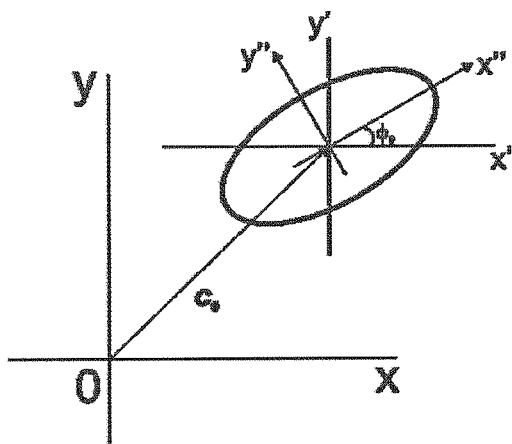
FIG. 15a is a definition of global (x, y) and local (x", y") coordinate systems for the rotated ellipse with offset $c_0$.

FIG. 15a is a definition of global (x, y) and local (x", y") coordinate systems for the rotated ellipse with offset $c_0$.

For an arbitrary offset $c_0$, this amounts to a translation $$\begin{pmatrix} x' \\ y' \end{pmatrix} = \begin{pmatrix} x \\ y \end{pmatrix} - \begin{pmatrix} c_{0x} \\ c_{0y} \end{pmatrix} \quad (71)$$

and a rotation $$\begin{pmatrix} x' \\ y' \end{pmatrix} = \begin{pmatrix} \cos\varphi_0 & -\sin\varphi_0 \\ \sin\varphi_0 & \cos\varphi_0 \end{pmatrix} \begin{pmatrix} x'' \\ y'' \end{pmatrix} = R_{x'x''} \begin{pmatrix} x'' \\ y'' \end{pmatrix} \quad (72)$$

The NV field of the scattering object is only affected by rotation. The product of NV components in Eq. (66) in the global (x, y)—and local (x", y")—system are related by a linear transformation $$\begin{pmatrix} n_x^2 \\ n_x n_y \\ n_y^2 \end{pmatrix} = \begin{pmatrix} \cos^2\varphi_0 & -2\sin\varphi_0\cos\varphi_0 & \sin^2\varphi_0 \\ \sin\varphi_0\cos\varphi_0 & (\cos^2\varphi_0 - \sin^2\varphi_0) & -\sin\varphi_0\cos\varphi_0 \\ \sin^2\varphi_0 & 2\sin\varphi_0\cos\varphi_0 & \cos^2\varphi_0 \end{pmatrix} \begin{pmatrix} (n_x'')^2 \\ n_x'' n_y'' \\ (n_y'')^2 \end{pmatrix}. \quad (73)$$

Combining Eqs. (71), (72) and (73), we can transform the $\Gamma_{ij}$ integral to $\Gamma''_{ij}$ as computed in the local coordinate system $$\begin{pmatrix} \Gamma_{xx} \\ \Gamma_{xy} \\ \Gamma_{yy} \end{pmatrix} = M_{nn''} \begin{pmatrix} \Gamma''_{xx} \\ \Gamma''_{xy} \\ \Gamma''_{yy} \end{pmatrix}. \quad (74)$$

where $M_{nn''}$ is the coupling matrix from Eq. (73) and $$\Gamma''_{ij}(m_1, m_2) = \quad (75)$$

$$\frac{e^{i[b_e \cdot c_0]}}{(a_{1x}a_{2y} - a_{1y}a_{2x})} \iint_{support} n_i'' n_j'' e^{i(k_{ex}(m_1,m_2)x'' + k_{ey}(m_1,m_2)y'')} dx'' dy'',$$

Here we have introduced the effective wave vectors $$\begin{pmatrix} k_{ex}(m_1, m_2) \\ k_{ey}(m_1, m_2) \end{pmatrix} = \begin{pmatrix} \cos\varphi_0 & \sin\varphi_0 \\ -\sin\varphi_0 & \cos\varphi_0 \end{pmatrix} \begin{pmatrix} b_{ex}(m_1, m_2) \\ b_{ey}(m_1, m_2) \end{pmatrix} \quad (76)$$

The $\Gamma''_{ij}$ integral is still computed over an area that is equal to the support of the contrast source (translation and rotation do not change that), but in the local coordinate system the integral is more easily evaluated—as we shall see—for the ellipse and the rectangle.

Summarizing, the effect of transforming to the local coordinate system is threefold:
- a constant phase factor to describe the effect of an offset
- an effective wave vector describing the orientation of the object with respect to the Bravais lattice
- $\Gamma'_{ij}$ becomes a linear combination of all three $\Gamma''_{ij}$ in the local coordinate system

3.3. The Ellipse

There are two well-known methods to generate the NV field of an ellipse, through the elliptic coordinate system $$r = \begin{pmatrix} a\cos\varphi \\ b\sin\varphi \end{pmatrix} = a\begin{pmatrix} \cos\varphi \\ e\sin\varphi \end{pmatrix}, \quad (77)$$

where a is the radius along the horizontal symmetry axis, b the radius along the vertical symmetry axis, $\varphi$ the azimuthal angle and e=b/a the ellipticity.

through the conformal mapping $$\begin{pmatrix} x \\ y \end{pmatrix} = \begin{pmatrix} a\cosh u \cos v \\ a\sinh u \sin v \end{pmatrix}. \quad (78)$$

For constant u ($0 \leq u < \infty$) and $0 \leq v \leq 2\pi$ this gives an elliptic contour.

Figure 15B:
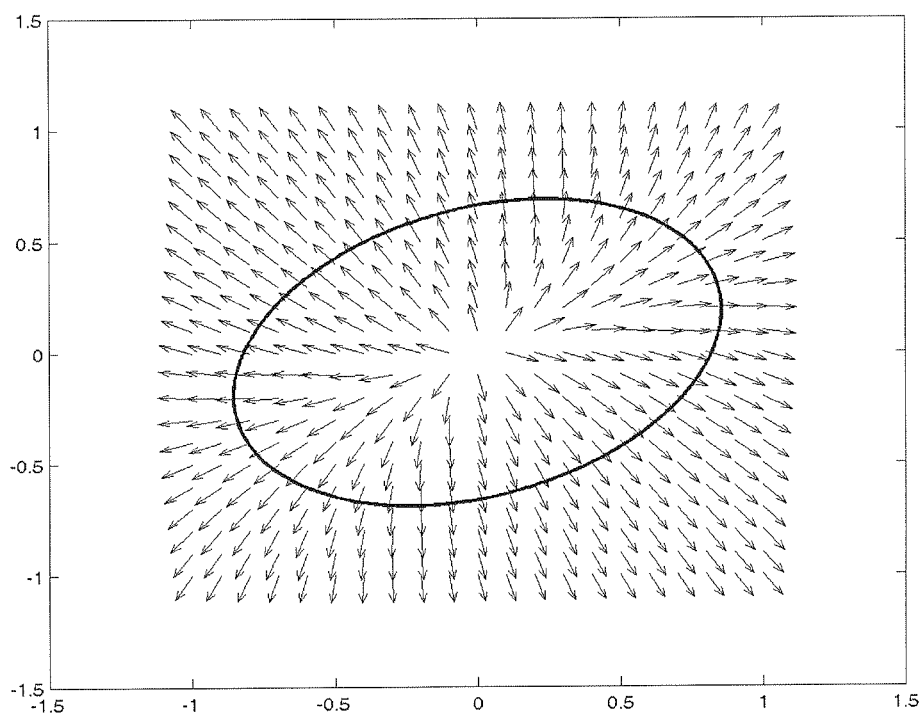
FIG. 15b illustrates a NV field for the elliptical coordinate system.
Figure 15C:
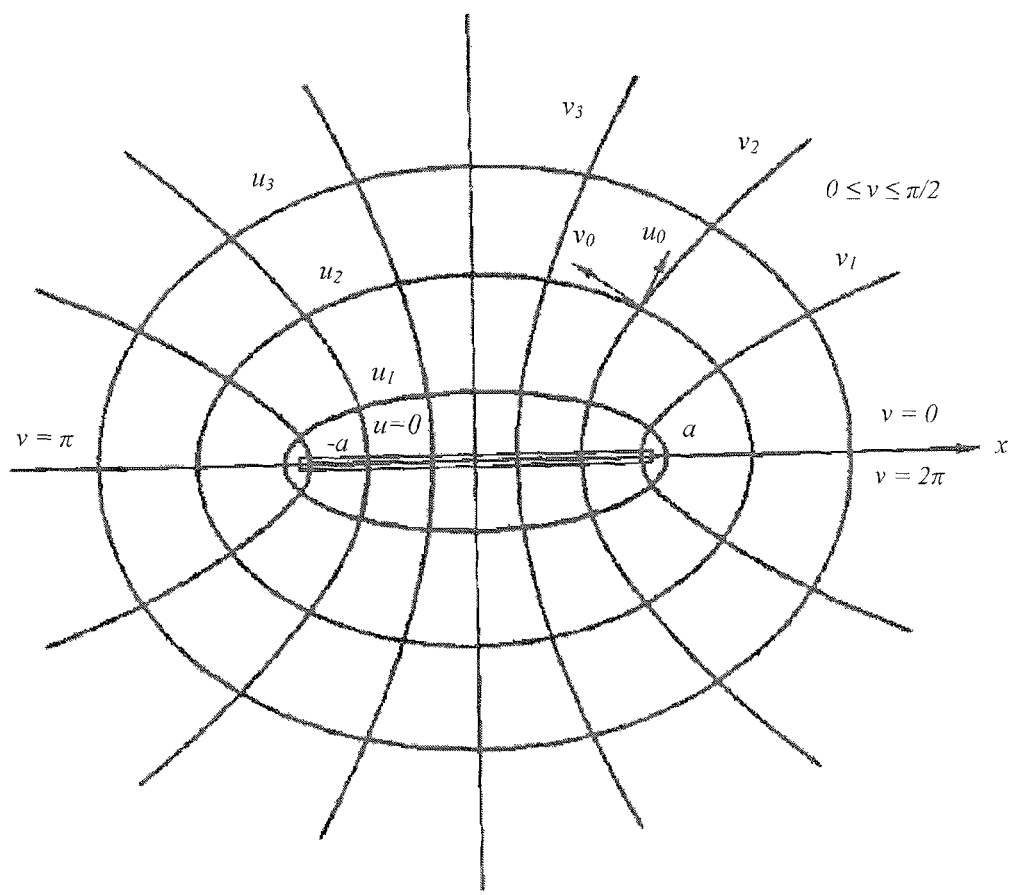
FIG. 15c illustrates conformal mapping for an ellipse.

FIG. 15b illustrates a NV field for the elliptical coordinate system and FIG. 15c illustrates conformal mapping.

The elliptic coordinate system has the advantage that an analytical expression for $\Gamma''_{ij}$ can be derived and that the normal-vector field only has a singularity at (0,0) while the conformal mapping has singular behavior over the line connecting the foci. We shall later see, for the case of the rectangle, that despite the presence of singularities good convergence can still be obtained. The presence of singularities alone is therefore not a convincing argument to reject a normal-vector field. The possibility to derive analytical expressions for the Fourier integral is a much stronger argument since it will result in fast computation of the matrix vector product. The normal-vector field can be derived as the vector perpendicular to the tangential vector $\partial r/\partial \varphi$ $$n = \frac{1}{\sqrt{e^2\cos^2\varphi + \sin^2\varphi}} \begin{pmatrix} e\cos\varphi \\ \sin\varphi \end{pmatrix}. \quad (79)$$

For this expression, we write the normal-vector products that are required for Eq. (66)

$$\begin{pmatrix} n_x^2(\varphi) \\ n_x n_y(\varphi) \\ n_y^2(\varphi) \end{pmatrix} = \frac{1}{e^2\cos^2\varphi + \sin^2\varphi} \begin{pmatrix} e^2\cos^2\varphi \\ e\cos\varphi\sin\varphi \\ \sin^2\varphi \end{pmatrix}. \quad (80)$$

Rewriting the $\Gamma''_{ij}$ integral to the elliptic coordinate system gives $$\Gamma''_{ij}(m_1, m_2) = \frac{e^{i[b_e \cdot c_0]}}{(a_{1x}a_{2y} - a_{1y}a_{2x})} \quad (81)$$

$$\int_0^a \int_0^{2\pi} n_i(\varphi)n_j(\varphi) e^{i(k_{ex}(m_1,m_2)r\cos\varphi + ek_{ey}(m_1,m_2)r\sin\varphi)} erdr d\varphi,$$

Fortunately, the r- and $\varphi$-dependence can be further separated from the Fourier exponent by using the identity [2, p. 973]

$$e^{iz\cos\varphi} = J_0(z) + 2\sum_{k=1}^{\infty} (-1)^k J_{2k}(z)\cos(2k\varphi) + \quad (82)$$

$$2i\sum_{k=0}^{\infty} (-1)^k J_{2k+1}(z)\cos[(2k+1)\varphi],$$

where $J_n(z)$ is the Bessel function of the first kind with integer order n. By rewriting the argument of the exponent in Eq. (81)

$$k_{ex}(m_1, m_2)r\cos\varphi + ek_{ey}(m_1, m_2)r\sin\varphi = \quad (83)$$

$$r\sqrt{(k_{ex}(m_1, m_2))^2 + (ek_{ey}(m_1, m_2))^2} \cos(\varphi - c)$$

where $c = \arctan\left(\frac{ek_{ey}(m_1, m_2)}{k_{ex}(m_1, m_2)}\right)$, the identity in Eq. (82) can be applied to the exponent in the integral in Eq. (81) resulting in the following expression for $\Gamma''_{xx}$ $$\Gamma''_{xx}(m_1, m_2) = \frac{e^{i[b_e \cdot c_0]}}{(a_{1x}a_{2y} - a_{1y}a_{2x})} \quad (84)$$

$$\left\{\int_0^a J_0(z)erdr \int_0^{2\pi} \frac{e^2\cos^2\varphi}{e^2\cos^2\varphi + \sin^2\varphi} d\varphi + 2\sum_{k=1}^{\infty}(-1)^k \right.$$

$$\int_0^a J_{2k}(z)erdr \int_0^{2\pi} \frac{e^2\cos^2\varphi}{e^2\cos^2\varphi + \sin^2\varphi}\cos[2k(\varphi - c)]d\varphi +$$

$$2j\sum_{k=0}^{\infty}(-1)^k \int_0^a J_{2k+1}(z)erdr$$

$$\left. \int_0^{2\pi} \frac{e^2\cos^2\varphi}{e^2\cos^2\varphi + \sin^2\varphi}\cos[(2k+1)(\varphi - c)]d\varphi \right\}$$

where $$z \equiv r\sqrt{(k_{ex}(m_1, m_2))^2 + (ek_{ey}(m_1, m_2))^2}. \quad (85)$$

The expressions for $\Gamma''_{xy}$ and $\Gamma''_{yy}$ can be obtained by replacing the numerator in the angular integrals by e sin $\varphi$ cos $\varphi$ resp. $\sin^2 \varphi$. The efficiency of this approach for the ellipse derives from the fact that analytical expressions for the radial and angular integrals can be found. These expressions for the radial integral of the Bessel function are derived in Appendix A. For the angular integrals they are derived in Appendix B, where they are labeled $\Phi_{ij}^e(k, \varphi_a, \varphi_b)$ and $\Phi_{ij}^o(k, \varphi_a, \varphi_b)$ for the angular integrals running from $\varphi_a$ to $\varphi_b$ for index k in resp. the summation over even and odd terms. For the full ellipse, the evaluation of Eq. (84) is simplified by the fact that $\Phi_{ij}^o(k, 0, 2\pi)=0$. The angular integral for the even terms is $$\left\{\begin{array}{l}\Phi_{xx}^e(k,0,2\pi)\\ \Phi_{xy}^e(k,0,2\pi)\\ \Phi_{yy}^e(k,0,2\pi)\end{array}\right\} = \left\{\begin{array}{l}\dfrac{2\pi e}{(1+e)^2}\cos(2kc)\left(\dfrac{1-e}{1+e}\right)^{k-1}\\ \dfrac{2\pi e}{(1+e)^2}\sin(2kc)\left(\dfrac{1-e}{1+e}\right)^{k-1}\\ -\dfrac{2\pi e}{(1+e)^2}\cos(2kc)\left(\dfrac{1-e}{1+e}\right)^{k-1}\end{array}\right\} \quad (86)$$

$$= \left\{\begin{array}{c}\dfrac{2\pi e}{1+e}\\ 0\\ \dfrac{2\pi}{1+e}\end{array}\right\} \quad \text{(for } k=0\text{)}. \quad (87)$$

Note that for the case of a circle (e=1) only the (k=1)-terms are non-zero.

The radial integrals need now only be evaluated for even order n. In Appendix A, a closed-form expression is derived for the indefinite integral $$\int^z z' J_{2n}(z')dz' = \quad (88)$$

$$-2nJ_0(z) + (-1)^n z J_1(z) - 4\sum_{m=1}^{n-1} J_{2m}(z)[n-(-1)^{n-m}m],$$

where the summation is only computed for n>1. Substituting Eqs (86) and (88) in Eq. (84) gives $$\Gamma_{xx}''(m_1,m_2) = \dfrac{e^{i[b_e\cdot c_0]}}{(a_{1x}a_{2y}-a_{1y}a_{2x})} \quad (89)$$

$$\left\{\begin{array}{l}\dfrac{ea^2}{R}J_1(R)\Phi_{xx}^e(k=0,0,2\pi) +\\ \dfrac{ea^2}{R^2}4[1-J_0(R)]\sum_{k=1}^{N_b}(-1)^k k\Phi_{xx}^e(k,0,2\pi) +\\ 2\dfrac{ea^2}{R}J_1(R)\sum_{k=1}^{N_b}\Phi_{xx}^e(k,0,2\pi) -\\ 8\dfrac{ea^2}{R^2}\sum_{m=1}^{N_b-1}J_{2m}(R)\\ \left[\sum_{k=m+1}^{N_b}(-1)^k k\Phi_{xx}^e(k,0,2\pi) - (-1)^m m\sum_{k=m+1}^{N_b}\Phi_{xx}^e(k,0,2\pi)\right]\end{array}\right\},$$

where $N_b$ is the number of terms that is retained in the summation over the even Bessel functions and $$R = a\sqrt{(k_{ex}(m_1,m_2))^2 + (ek_{ey}(m_1,m_2))^2}. \quad (90)$$

Note that in the last term the summations over k and in have been swapped to prevent multiple evaluations of Bessel functions of the same argument. For the computation of $\Gamma''_{xy}$ and $\Gamma''_{yy}$, $\Phi_{xx}^e$ only needs to be substituted by the expressions for $\Phi_{xy}^e$ and $\Phi_{yy}^e$ (see Appendix B).

3.4. The Rectangle

The generation of a continuous NV field for the rectangle is less obvious than for the ellipse. It has been proposed [3] to use the Schwartz-Christoffel transformation for this purpose [4]. A NV field that closely approximates this solution for the rectangle is $$\begin{pmatrix}n_x\\ n_y\end{pmatrix} = \begin{pmatrix}x\sqrt{b^2-y^2}\\ y\sqrt{a^2-x^2}\end{pmatrix}. \quad (91)$$

Figure 16A:
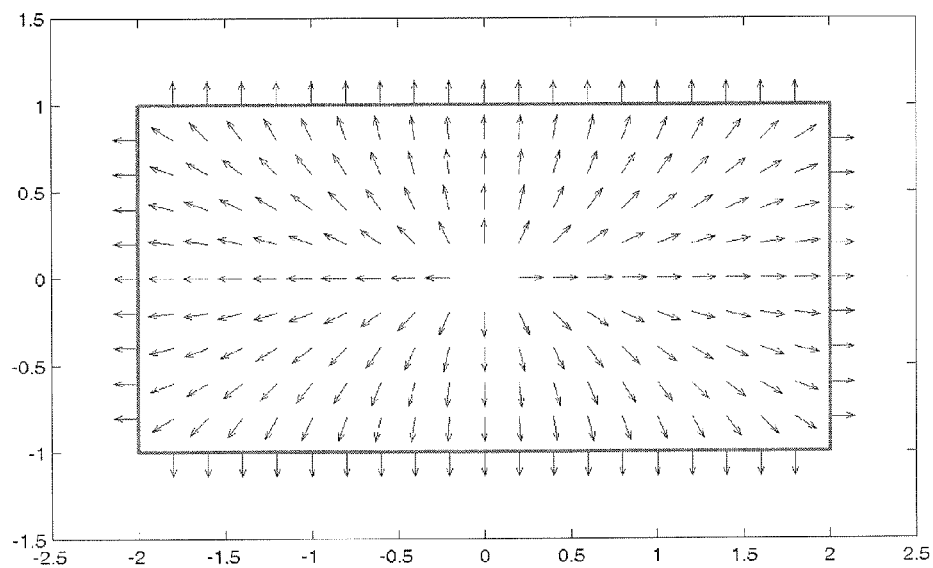
FIG. 16a illustrates continuous NV field for the rectangle.

FIG. 16a illustrates a corresponding continuous NV field for the rectangle. This expression, however, does not lend itself for deriving an analytical expression of the $\Gamma_{ij}$ integral. For this case, we choose to derive a NV field that closely resembles Eq. (91), but is discontinuous along the diagonals of the rectangle, constant within the triangles formed by the diagonals, and normal to the edges of the rectangle.

Figure 16B:
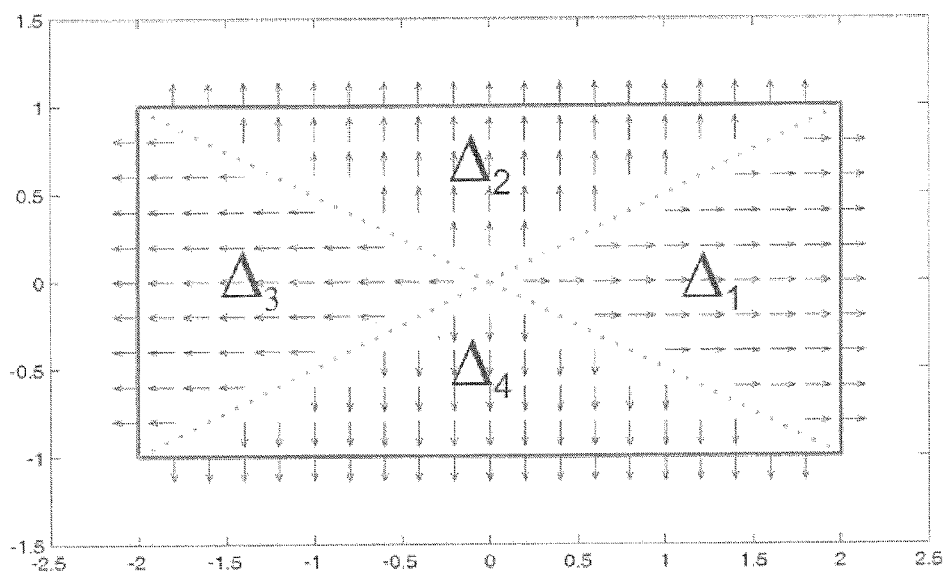
FIG. 16b illustrates discontinuous NV field for the rectangle.

FIG. 16b illustrates a corresponding discontinuous NV field for the rectangle. This normal-vector field is constant for each triangle which makes the $\Gamma''_{ij}$ integral particularly simple to calculate.

$$\Gamma_{ij}''(m_1,m_2) = \quad (92)$$

$$\dfrac{e^{i(b_e\cdot c_0)}}{(a_{1x}a_{2y}-a_{1y}a_{2x})}n_i n_j \int_{\Delta_1\Delta_2}\int_{\Delta_3\Delta_4} e^{i(k_{ex}(m_1,m_2)x + k_{ey}(m_1,m_2)y)}dxdy.$$

The evaluation of the surface integral is straightforward. For triangle $\Delta_1$ (see FIG. 16b) it gives $$\int_{\Delta_1}\ldots = r_a e^{\frac{1}{2}ik_{ex}r_a}\dfrac{1}{ik_{ey}}\left[e^{\frac{1}{2}ik_{ey}r_b}\text{sinc}\left(\dfrac{1}{2}k_{ex}r_a + \dfrac{1}{2}k_{ey}r_b\right) - e^{-\frac{1}{2}ik_{ey}r_b}\text{sinc}\left(\dfrac{1}{2}k_{ex}r_a - \dfrac{1}{2}k_{ey}r_b\right)\right]. \quad (93)$$

For triangle $\Delta_2$ we only need to swap $r_a \leftrightarrow r_b$ and $k_{ex} \leftrightarrow k_{ey}$. The result for triangles $\Delta_3$ and $\Delta_4$ is simply the complex conjugate of the integral for resp. $\Delta_1$ and $\Delta_2$.

For the NV field $\Gamma_{xx}=0$ for triangles $\Delta_2$ and $\Delta_4$, $\Gamma_{yy}=0$ for triangles $\Delta_1$ and $\Delta_3$ and $\Gamma_{xy}=\Gamma_{yx}=0$ for all triangles. Note that for the limit $k_{ey}\to 0$ Eq. (93) becomes $$\lim_{k_{ey}\to 0}\int_{\Delta_1}\ldots = \quad (94)$$

$$r_a r_b e^{\frac{1}{2}ik_{ex}r_a}\left[\text{sinc}\left(\dfrac{1}{2}k_{ex}r_a\right) - i\left(\dfrac{\cos\left(\frac{1}{2}k_{ex}r_a\right) - \text{sinc}\left(\frac{1}{2}k_{ex}r_a\right)}{\frac{1}{2}k_{ex}r_a}\right)\right].$$

4. Cut-and-Connect Strategy

The previous section on the NV field generation for the rectangle, shows a very powerful method for generating the NV field for more arbitrary shapes. These shapes can be decomposed in elementary shapes for which the $\Gamma_{ij}$ integral has a closed form suited for fast computation. By summing up the relevant $\Gamma_{ij}$ integrals for each elementary shape at a particular Fourier mode index, the spectral representation of $C_\epsilon$ and $\epsilon C_\epsilon$ can be easily obtained. Of course, the class of elementary shapes must be large enough to generate all relevant more complex shapes. The class of elementary shapes comprises: (A) triangles with a constant NV field: if one interface is a material interface, the NV field must be perpendicular to this interface. If there is no material interface, the NV field can be chosen arbitrarily; (B) trapezoids with a constant NV field (the rectangle is a special case): if one interface is a material interface, the NV field must be perpendicular to this interface. If there is no material interface, the NV field can be chosen arbitrarily; or (C) circle segment with a radial NV field and material interface along the circle edge.

Any arbitrary shape—or approximation thereof—can in principle be decomposed in a mesh of these elementary shapes.

Figure 17:
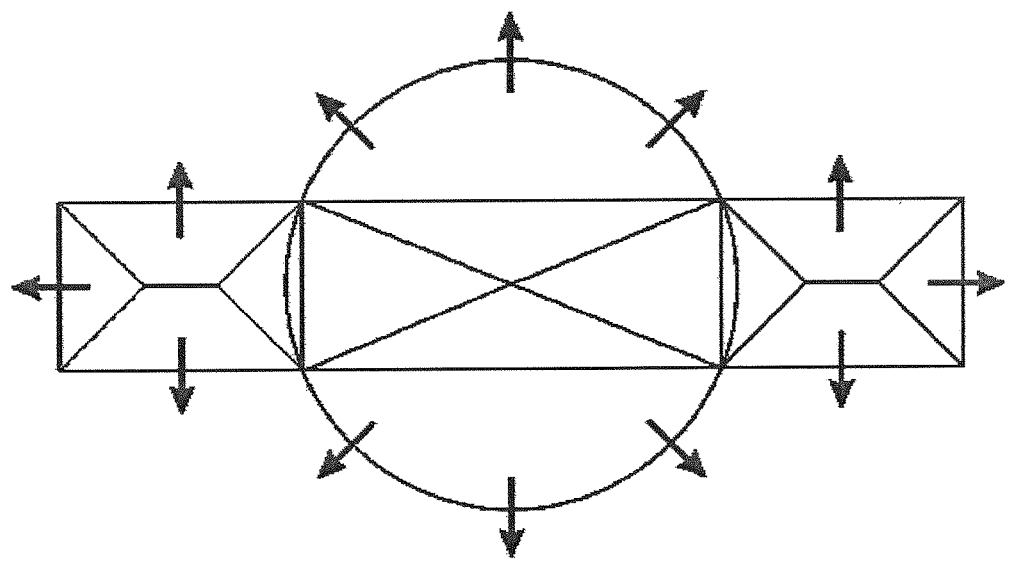
FIG. 17 illustrates meshing a 'dogbone' in elementary shapes.

FIG. 17 illustrates meshing a 'dogbone' in these elementary shapes.

Figure 18:
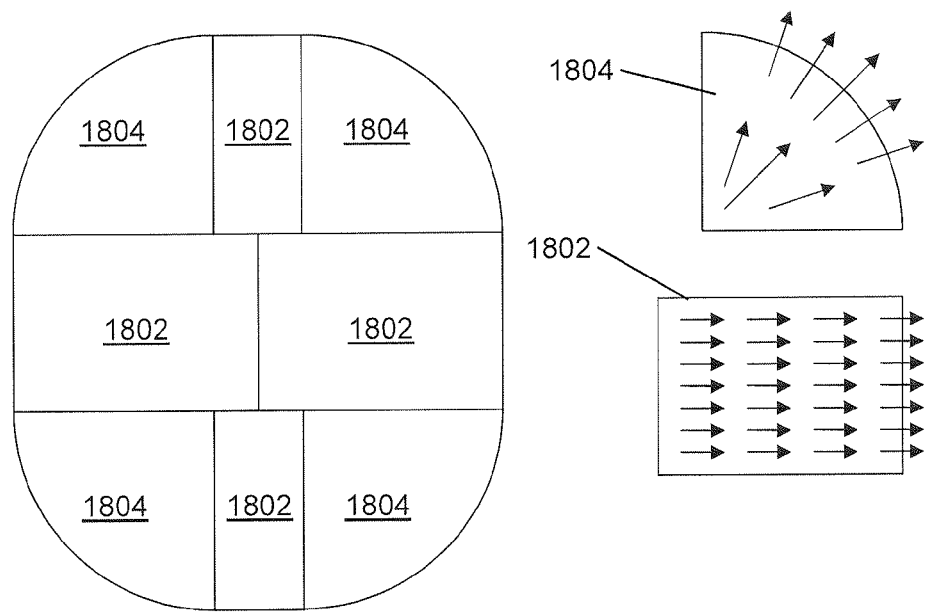
FIG. 18 illustrates building the normal-vector field of a prism with a cross section of a rounded rectangle from smaller rectangles and circle segments in accordance with an embodiment of the present invention.

FIG. 18 illustrates building the normal-vector field of a prism with a cross section of a rounded rectangle from smaller rectangles 1802 and circle segments 1804 in accordance with an embodiment of the present invention. Note that the normal-vector field shown by the arrows is perpendicular to the physical interfaces at those physical interfaces.

In an embodiment of the present invention, there is provided a method to construct a normal-vector field locally (i.e. over the scattering object or parts thereof) instead of over the entire unit cell. This simplifies the generation of a normal-vector field and even gives mathematically very simple expressions for basic shapes like circles, ellipses and rectangles.

For more complicated shapes, a cut-and-paste meshing technique is provided where the normal-vector field of an arbitrary shape is composed of the normal-vector fields of two or more elementary shapes selected from: a prism with the following cross section: a triangle; a rectangle; a trapezoid; or a circular segment; a tetrahedron; a bar; a hexahedron with two parallel faces; an apex truncated pyramid with truncation face parallel to the ground plane; and spherical segment.

For these building blocks, the normal-vector field can be very simply and rapidly generated.

Alternatively, for other complicated shapes, it may be advantageous to generate a normal-vector field directly from the shape, without applying the above meshing strategy to avoid a high mesh density. This results in the use of interpolation methods to generate normal-vector fields, which are then used to compute certain Fourier integrals. An embodiment of the present invention breaks up the Fourier integrals into several integrals over the support of the various media in the computational domain. For each of these domains, dedicated quadrature rules are applied in combination with an interpolation algorithm to generate the normal-vector field on this domain. Interpolation is applied based on basis functions with periodic continuation, to avoid artificial discontinuities in the integrants, due to a particular choice for the boundaries of unit cell. Further, it is possible to further limit the support of the normal-vector field to a direct neighborhood of a material interface. This leads to an even more parsimonious approach to generate normal-vector fields for more complicated shapes.

4.1. Elementary Building Blocks

In this section, closed expressions for the $\Gamma_{ij}$ integral will be derived for the three elementary building blocks expressed in the coordinates of the shape vertices.

4.2. The Triangle

Figure 19:
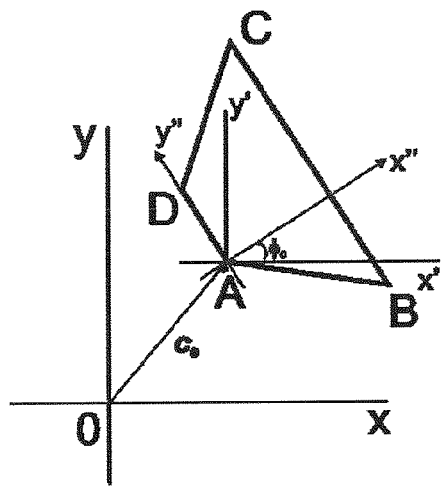
FIG. 19 illustrates rotated and shifted triangle with NV field and local coordinate system.

FIG. 19 illustrates rotated and shifted triangle with NV field and local coordinate system.

FIG. 19 shows an arbitrary triangle with vertices A, B and C. The vertex opposite to the material interface, (B-C), is chosen as the local origin. Note that the vertices are ordered in a counterclockwise direction. First we translate over vector A to obtain vectors B'=(B−A) and C'=(C−A). Then we rotate over angle $\phi_0$ to get to the local coordinate system. In this system, B" and C" are given by Eq. (72)

$$\begin{Bmatrix} B'' \\ C'' \end{Bmatrix} = \begin{pmatrix} \cos\varphi_0 & \sin\varphi_0 \\ -\sin\varphi_0 & \cos\varphi_0 \end{pmatrix} \begin{Bmatrix} B' \\ C' \end{Bmatrix}, \quad (95)$$

where $$\cos\varphi_0 \equiv \frac{(C_y - B_y)}{\sqrt{(C_x - B_x)^2 + (C_y - B_y)^2}} \quad \text{and} \quad (96)$$

$$\sin\varphi_0 \equiv \frac{-(C_x - B_x)}{\sqrt{(C_x - B_x)^2 + (C_y - B_y)^2}}.$$

With the expressions for the coordinates of B" and C", we obtain $$\Gamma_{ij}''(m_1, m_2) = \frac{e^{i(b_e \cdot A)}}{(a_{1x}a_{2y} - a_{1y}a_{2x})} n_i n_j \quad (97)$$

$$\int_0^{b_x} e^{ik_{ex}(m_1, m_2)x''} \int_{\left(\frac{b_y}{b_x}\right)x''}^{\left(\frac{c_y}{c_x}\right)x''} e^{ik_{ey}(m_1, m_2)y''} dy'' dx'' =$$

$$\frac{e^{i(b_e \cdot A)}}{(a_{1x}a_{2y} - a_{1y}a_{2x})} n_i n_j \frac{b_x}{ik_{ey}} e^{\frac{1}{2}ik_{ex}b_x} \left( e^{\frac{1}{2}ik_{ey}c_y} \text{sinc} \right.$$

$$\left. \left[\frac{1}{2}(k_{ex}b_x + k_{ey}c_y)\right] - e^{\frac{1}{2}ik_{ey}b_y} \text{sinc} \left[\frac{1}{2}(k_{ex}b_x + k_{ey}b_y)\right] \right)$$

In case B"C" is a material interface, the NV field is $(n_x'', n_y'')=(1,0)$ leaving only $\Gamma''_{xx}$ as a non-zero component. $\Gamma_{ij}$ in the global coordinate system is obtained through Eq. (74).

4.3. The Trapezoid

Figure 20:
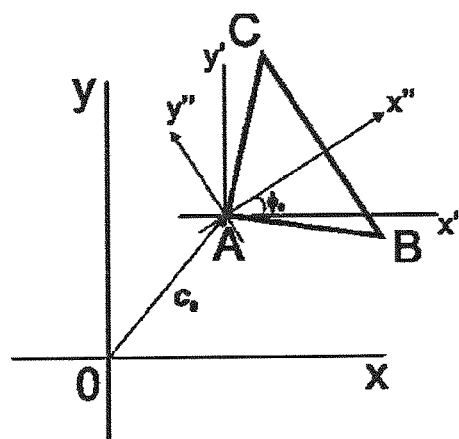
FIG. 20 illustrates a rotated and shifted trapezoid with NV field and local coordinate system.

FIG. 20 illustrates a rotated and shifted trapezoid with NV field and local coordinate system.

For the trapezoid, the same line of reasoning can be followed. First, the coordinates are translated over A giving $$\begin{Bmatrix} B' \\ C' \\ D' \end{Bmatrix} = \begin{Bmatrix} B - A \\ C - A \\ D - A \end{Bmatrix} \quad (98)$$

and subsequently rotated over $\phi_0$ to give $$\begin{Bmatrix} B'' \\ C'' \\ D'' \end{Bmatrix} = \begin{pmatrix} \cos\varphi_0 & \sin\varphi_0 \\ -\sin\varphi_0 & \cos\varphi_0 \end{pmatrix} \begin{Bmatrix} B' \\ C' \\ D' \end{Bmatrix}, \quad (99)$$

where $$\cos\varphi_0 \equiv \frac{(C_y - B_y)}{\sqrt{(C_x - B_x)^2 + (C_y - B_y)^2}} \quad \text{and} \quad (100)$$

$$\sin\varphi_0 \equiv \frac{-(C_x - B_x)}{\sqrt{(C_x - B_x)^2 + (C_y - B_y)^2}}.$$

In the local coordinate system $$\Gamma_{ij}''(m_1, m_2) = \frac{e^{i(b_e \cdot A)}}{(a_{1x}a_{2y} - a_{1y}a_{2x})} n_i n_j \quad (101)$$

-continued $$\int_0^{b_x} e^{ik_{ex}(m_1,m_2)x''} \int_{\left(\frac{b_y}{b_x}\right)x''}^{d_y + \left(\frac{c_y-d_y}{c_x}\right)x''} e^{ik_{ey}(m_1,m_2)y''} dy'' dx'' =$$

$$\frac{e^{i(b_e \cdot A)}}{(a_{1x}a_{2y} - a_{1y}a_{2x})} n_i n_j \frac{b_x}{ik_{ey}}$$

$$e^{\frac{1}{2}ik_{ex}b_x}\left(e^{\frac{1}{2}ik_{ey}(c_y+d_y)}\mathrm{sinc}\left[\frac{1}{2}(k_{ex}b_x + k_{ey}(c_y - d_y))\right] - \right.$$

$$\left. e^{\frac{1}{2}ik_{ey}b_y}\mathrm{sinc}\left[\frac{1}{2}(k_{ex}b_x + k_{ey}b_y)\right]\right)$$

This result can also be obtained by decomposing the trapezoid in two triangles and adding Eq. (97) for both triangles. Also for the trapezoid the NV field is $(n_x'', n_y'')=(1,0)$ in case B"C" is a material interface, leaving only $\Gamma''_{xx}$ as a non-zero component. $\Gamma_{ij}$ in the global coordinate system is obtained through Eq. (74).

4.4. The Circle Segment

The circle segment is defined as a section from a circle with origin A, lower radius endpoint B and section angle $\phi_s$.

Figure 21:
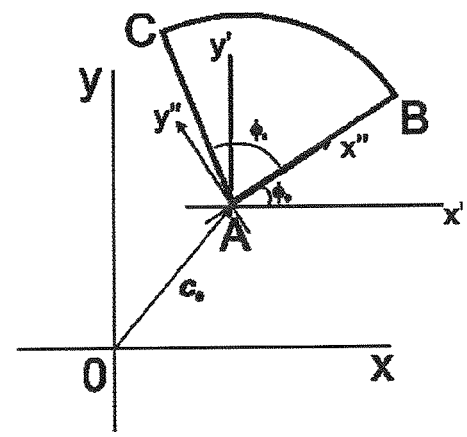
FIG. 21 illustrates rotated and shifted circle segment with NV field and local coordinate system.

FIG. 21 illustrates rotated and shifted circle segment with NV field and local coordinate system.

The NV component $\Gamma_{ij}$ can be computed along the same lines as for the full ellipse in Section 3.3. The main difference is that the angular integrals are now evaluated from 0 to an arbitrary angle $\phi_s$. This has the effect that the angular integral over the odd terms in the Bessel summation $\Phi_{ij}^o(k, 0, \phi_s) \neq 0$. Also for the odd terms, the radial integral over the Bessel function has an analytical expression (see Appendix A)

$$\int^z z' J_{2n+1}(z') dz' = (2n+1)\int^z J_0(z') dz' - \quad (102)$$

$$(-1)^n z J_0(z) - 2\sum_{m=1}^n J_{2m-1}(z)[(2n+1) + (-1)^{n-m}(2m-1)],$$

where the summation only applies to the case $n \geq 1$. Substitution of Eq. (102) in Eq. (84) gives $$\Gamma''_{xx}(m_1, m_2) = \quad (103)$$

$$\frac{e^{i[b_e \cdot c_0]}}{(a_{1x}a_{2y} - a_{1y}a_{2x})} \left\{ \frac{ea^2}{R} J_1(R)\Phi^e_{xx}(k=0, 0, \phi_s) + \frac{ea^2}{R^2} 4[1 - J_0(R)] \right.$$

$$\sum_{k=1}^{N_b}(-1)^k k\Phi^e_{xx}(k, 0, \phi_s) + 2\frac{ea^2}{R}J_1(R)\sum_{k=1}^{N_b}\Phi^e_{xx}(k, 0, \phi_s) -$$

$$8\frac{ea^2}{R^2}\sum_{m=1}^{N_b-1}J_{2m}(R)\left[\sum_{k=m+1}^{N_b}(-1)^k k\Phi^e_{xx}(k, 0, \phi_s) - (-1)^m m\right.$$

$$\left.\sum_{k=m+1}^{N_b}\Phi^e_{xx}(k, 0, \phi_s)\right] - 2i\frac{ea^2}{R}J_0(R)\sum_{k=0}^{N_b}\Phi^o_{xx}(k, 0, \phi_s) +$$

$$4i\frac{ea^2}{R^2}\left(\sum_{p=0}^{N_b}J_{2p+1}(R)\right)\sum_{k=0}^{N_b}(-1)^k(2k+1)\Phi^o_{xx}(k, 0, \phi_s) -$$

$$4i\frac{ea^2}{R^2}\sum_{m=1}^{N_b}J_{2m-1}(R)\left[\sum_{k=m}^{N_b}(-1)^k(2k+1)\Phi^o_{xx}(k, 0, \phi_s) + \right.$$

$$\left. (-1)^m(2m-1)\sum_{k=m}^{N_b}\Phi^o_{xx}(k, 0, \phi_s)\right]\right\}$$

where $N_b$ is the number of terms that is retained in the summation over the even Bessel functions and $$R = a\sqrt{(k_{ex}(m_1,m_2))^2 + (ek_{ey}(m_1,m_2))^2}. \quad (104)$$

The primitive of $J_0$ has been rewritten using ([2, p. 633])

$$\int^z J_k(z') dz' = 2\sum_{p=0}^\infty J_{k+2p+1}(z). \quad (105)$$

For $\Gamma''_{xy}$ and $\Gamma''_{yy}$, the NV components can be easily found by substituting the appropriate expressions for the angular integrals (see Appendix B).

5. Generation of Normal-Vector Fields for More General Shapes

For certain situations, e.g., cases with exotic scattering geometries or cases where multiple materials have connecting interfaces between each other, it may be difficult to apply a meshing strategy that leads to a low number of meshing elements and that exhibits rapid convergence in the spectral base of the electric field and electric flux density. For such cases, a more general approach may be needed to generate the Fourier coefficients of the field-material interaction operators. One such approach is to employ numerical quadrature to evaluate the integrals of the form (54). A quadrature rule then invokes the function values of the integrant at a number of points to arrive at an approximation of the desired integral. If we take a look at the integrants under consideration, we notice that we need to evaluate the permittivity, the exponential function, and the Cartesian components of the normal-vector field at an arbitrary (x, y) point. This is trivial for the former two functions, but non-trivial for the latter. Owing to the scaling introduced earlier on, the normal-vector field is only needed in regions where $\alpha \epsilon \neq 1$. Further, we note that the Fourier coefficients for all Fourier indices $(m_1, m_2)$ can be obtained via the same quadrature rule and function evaluations, except that the exponential function is evaluated for all Fourier indices. Therefore, the main concern is to evaluate the normal-vector field at an arbitrary position (assuming that $\alpha \epsilon \neq 1$).

Several recipes to generate normal-vector fields have been discussed in [3,5]. The first article discusses the generation of two-dimensional normal-vector fields within the context of RCWA based on Schwarz-Christoffel conformal mappings or via solving an electrostatic problem. The second article discusses the generation via the inverse-distance interpolation algorithm, which is a particular example of a so-called scattered-data interpolation algorithm with radial basis functions. However, both articles teach generating the normal-vector field on a regular grid, without taking into account the possibility that normal-vector field may only be needed locally. Further, regular grids may yield slow convergence for permittivity profiles that do not fit to this regular grid, i.e. for piecewise constant material properties with interfaces that do not coincide with the regular mesh. Consequently, a very large number of grid points may be needed to reach a converged solution. These two observations make these procedures extremely expensive in terms of CPU time.

According to an embodiment of the present invention, we use localized normal-vector fields and apply quadrature rules that take into account the domain of integration of the scattering object, i.e. work with integration domains that take into account the shape of the material interfaces. As a consequence, the integration over the unit cell is replaced by a sequence of integrations over domains that have constant permittivity. Quadrature rules that integrate over more complicated domains have been studied in e.g., [6,7,8]. Since the permittivity per domain of integration is constant and the exponential function is continuous, the only possible hurdle is again the normal-vector field. Hence, to maintain the convergence of the quadrature rule, we need to generate a sufficiently smooth normal-vector field over the integration domain of the quadrature rule. This can be achieved by a scattered-data interpolation algorithm, for which the input data is generated from a description of the boundary of the integration domain and a corresponding normal-vector field at this boundary. For example, if the boundary is described by a piecewise linear approximation, then the normal is locally a constant vector. By providing a sufficiently dense sampling of the normal-vector field along the boundary, sufficient data is generated to apply a scattered-data interpolation algorithm.

5.1. Periodic Continuation of Normal-Vector Fields

Standard scattered-data interpolation algorithms use so-called radial basis functions, i.e. basis functions that only depend on the distance between a data point and the interpolation point. In a general interpolation problem, this is usually a good idea, since it allows nearby data to have a higher impact on the interpolated data as compared to data far away. However, in a periodic environment, the distance between a data point and an interpolation point also becomes periodic. If we do not take this into account, the interpolation across a periodic boundary can introduce artificial discontinuities, which may deteriorate the convergence of certain quadrature rules or even the convergence of the solution of the electromagnetic fields projected on the normal-vector field. Therefore, we look for alternatives for the scattered-data interpolation with radial basis functions. The key idea is to generate a periodic-distance function that exhibits the periodicity of the configuration and to let this function replace the distance function.

5.2. Periodic Distance Functions

In the regular Euclidean space $\mathbb{R}^3$, the distance r between two points r and r' is given by $$r = \sqrt{(x-x')^2 + (y-y')^2 + (z-z')^2}, \tag{106}$$

which is non-negative and only zero when the two points coincide.

Let us now first consider a 1D periodic case along the x-axis with period p>0. For such a case, we first introduce the modulo(p) function as $$x \bmod p = x - \left\lceil \frac{x}{p} \right\rceil p - \frac{p}{2}, \tag{107}$$

where $\lceil . \rceil$ denotes the ceiling operator. Hence, we have $$-\frac{p}{2} \leq x \bmod p < \frac{p}{2}. \tag{108}$$

With the above definition, the Euclidean distance d(x,x') =|x−x'| between x and x' becomes $d_p(x,x')=|(x-x') \bmod p|$, for the periodic case. However, there are also other ways to define a distance measure, e.g., $$d_p(x, x') = \left|\sin\left(2\pi \frac{x-x'}{p}\right)\right| \tag{109}$$

also satisfies the basic criteria for a distance measure d(x,x'), i.e.

1. d(x,x')≥0 (non-negative),
2. d(x,x')=0 if and only if x=x' (identity of indiscernibles)
3. d(x,x')=d(x',x) (symmetry),
4. d(x,x'')≤d(x,x')+d(x',x'') (triangle inequality).

For a space with two directions of periodicity, the situation is more complicated. Let us denote the periodic lattice vectors by $a_1$ and $a_2$ then we can indicate any point r=(x, y, z) in space as $$r = xu_x + yu_y + zu_z = \eta_1 a_1 + \eta_2 a_2 + zu_z, \tag{110}$$

where $\eta_1$ and $\eta_2$ are the coordinates in the transverse plane that relate to x and y as $$\begin{pmatrix} x \\ y \end{pmatrix} = \begin{pmatrix} (u_x, a_1) & (u_x, a_2) \\ (u_y, a_1) & (u_y, a_2) \end{pmatrix} \begin{pmatrix} \eta_1 \\ \eta_2 \end{pmatrix}. \tag{111}$$

Further, we note that the scattering configuration in periodic in $\eta_1$ and $\eta_2$, both with period 1. The Euclidean distance function in $\mathbb{R}$ can be expressed in $a_1$ and $a_2$ as $$d(r, r') = \sqrt{(r-r', r-r')} \tag{112}$$
$$= \sqrt{(\eta_1 - \eta_1')^2 \|a_1\|^2 + (\eta_2 - \eta_2')^2 \|a_2\|^2 + 2(\eta_1 - \eta_1')(\eta_2 - \eta_2')(a_1, a_2) + (z-z')^2}.$$

To arrive at a periodic distance function, we now replace $\eta_1 - \eta_1'$ and $\eta_2 - \eta_2'$ by a periodic function $f(\cdot)$ with period 1 and $f(0)=0$, such that $|f(\cdot)|$ gives rise to a one-dimensional periodic distance functions, i.e.

$$d_p(r, r') = \sqrt{f(\eta_1 - \eta_1')^2 \|a_1\|^2 + f(\eta_2 - \eta_2')^2 \|a_2\|^2 + 2f(\eta_1 - \eta_1')f(\eta_2 - \eta_2')(a_1, a_2) + (z-z')^2}, \tag{113}$$

where $f(x)$ is for example equal to x mod 1 or $\sin(2\pi x)$.

5.3. Periodic Scattered-Data Interpolation

In a scattered-data interpolation algorithm, a basis function $\phi(r)$, r≥0, is introduced, e.g., $\phi(r)=\exp(-\beta r^2)$ with β>0. Further, a set of data points $r_n$ and corresponding functions values $F(r_n)$, n∈{1, . . . , N} are provided. Then, the algorithms determines coefficients $c_n$ such that $$F(r_n) = \sum_{m=1}^{N} c_n \varphi(d(r_m, r_n)), \tag{114}$$

for all n=1, . . . , N, where $d(r_m, r_n)$ denotes the distance between the data points $r_m$ and $r_n$. If this set of linear equations is non-singular, the coefficients $c_n$ can be determined and the scattered-data interpolation algorithm leads to the following interpolation of F $$F(r) \approx \sum_{n=1}^{N} c_n \varphi(d(r, r_n)). \tag{115}$$

For the periodic case, we substitute the distance function $d(\bullet,\bullet)$ in the above two formulas by the periodic distance function in Eq. (113), and we arrive at a periodic interpolation of the data, which can be used to generate the Cartesian components of the normal-vector field from the Cartesian components of the normal-vectors fields at the material boundaries, in a similar way as in [5], i.e. we first find the interpolated components as $$\tilde{n}_j(r) = \sum_{i=1}^{N} c_{i,j} n_j(r_i) \varphi(d_p(r, r_i)), \tag{116}$$

where $j \in \{x, y, z\}$. Then we normalize the normal-vector field at position r to 1, i.e. $n(r) = \tilde{n}(r)/\|\tilde{n}(r)\|$.

6. Localized Normal-Vector Fields in Arbitrary Anisotropic Media

In the preceding sections, the concept of localized normal-vector fields in the construction of a continuous vector field F was achieved by introducing a scaling function and a basis transformation in the vector field defined by Popov and Nevière. The localization of the normal-vector field was demonstrated for isotropic media and for birefringent media with a fixed extra-ordinary axis that is orthogonal to the normal-vector field everywhere, e.g., due to a staircase approximation of the geometry of the grating. The concept of localized normal-vector fields will now be carried over to the most general case of arbitrary anisotropic media. However, scaling by a scalar function is not sufficiently flexible to deal with the most general case. To tackle the case of general anisotropic media, we start by modifying the definition of the vector field F. This renewed definition of F is given by $$F = P_T E + \alpha P_n (D - S P_T E), \tag{117}$$

where S is a additional scaling operator and $\alpha$ is a non-zero scaling function, which are both continuous in the vicinity of material discontinuities. Since both $P_n D$ and $P_T E$ are continuous vector fields, the vector field F is again continuous under the requirements for $\alpha$ and S.

With the previously outlined algebra for the projection operators, we obtain $$E = \left\{ I + (P_n M_\varepsilon P_n)^{-1} \left[ P_n \left( \frac{1}{\alpha} I - S \right) P_n - P_n (M_\varepsilon - S) \right] \right\} F. \tag{118}$$

The operator between square brackets can be made zero locally, for example by choosing $S = M_{\varepsilon_j}$, i.e. equal to the medium parameters in a certain area that does not involve discontinuities (e.g., a constant permittivity tensor of the filling medium), and by choosing $\alpha P_n = (P_n S P_n)^{-1}$ (to be understood on the range of $P_n$), which is a non-zero continuous function owing to the choice for S. For $\alpha$, this amounts to $\alpha = 1/(n, Sn)$. Hence in a region where $M_\varepsilon = M_{\varepsilon_j}$ holds, the normal-vector field is not required, provided the basis of the vector field F is independent of the normal-vector field, e.g., it is expressed in Cartesian coordinates. Another choice for S is to use a smoothed version of the permittivity distribution. For this choice, the region where the normal-vector field is required is shrunk even further.

For isotropic media, the above modification of the vector field F is consistent with the previous definition, since S will then be a multiple of the identity operator and hence it will commute with $P_T$ and $P_n$. Consequently, $P_n S P_T$ is identically zero and the choice for $\alpha$ reduces to the previously defined cases.

The main merits of the localized normal-vector field, i.e. the possibility to pre-compute expressions of the coefficients for the operators $C_\epsilon$ and $\epsilon C_\epsilon$ for each object separately and the possibility to apply the cut-and-connect strategy, are still valid in the general anisotropic case. However, the coefficients of the operators are typically more complicated, since the directions of anisotropy mixes with the direction on the normal-vector field. This can for example be observed from the operator $(P_n M_\epsilon P_n)^{-1}$, which was independent of the normal-vector field for isotropic media, whereas it does depend on the normal-vector field and the direction of the anisotropy in the general case. Therefore, finding closed-form expressions for the Fourier integrals that define the coefficients is typically harder and a quadrature approach as outlined in Section 5 can be a useful alternative. A notable exception is the case where the anisotropy of an object is constant over the support of the object and the shape of the object is described by mesh elements with a fixed direction of the normal-vector field, e.g., the triangular or polygonal mesh elements. For this case, the derived closed-form expressions remain valid, except for a constant scaling factor that depends on the angle between the (constant) normal vector field and the (constant) directions of the anisotropy of the permittivity tensor.

We have described a projection operator framework to analyze the concept of localized normal-vector fields within field-material interactions in a spectral basis, in isotropic and anisotropic media, which may be used in for example RCWA, the Differential Method, and the Volume-Integral Method. With this framework, we have been able to demonstrate that a scaling and basis transformations can lead to the localized normal-vector fields, which enable us to work with normal-vector fields for dedicated shapes and to apply a meshing strategy to construct normal-vector fields for more general shapes. This greatly improves the flexibility of the normal-vector field approach and also leads to significant saving of CPU time to set up these fields. We have illustrated the examples of closed-form solutions for a number building blocks and the generation of vector fields for more general shapes, including a periodic-distance interpolation algorithm.

Embodiments of the present invention allow for a faster and more flexible setup of normal-vector fields in 2D and 3D, which results in faster CD reconstruction times and faster library recipe generation. For a simple example, we have observed speed up from several minutes to sub-seconds on the same computing hardware.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The methods according to embodiments of the present invention described above may be incorporated into the forward diffraction model for reconstructing an approximate structure of an object (not limited to 1D-periodic) from a detected electromagnetic scattering property, such as a diffraction pattern, arising from illumination of the object by radiation, as described above with reference to FIGS. 5 and 6. The processing unit PU described above with reference to FIGS. 3 and 4 may be configured to reconstruct an approximate structure of an object using this method.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The term "electromagnetic" encompasses electric and magnetic.

The term "electromagnetic scattering properties" encompasses reflection and transmission coefficients and scatterometry measurement parameters including spectra (such as intensity as a function of wavelength), diffraction patterns (intensity as a function of position/angle) and the relative intensity of transverse magnetic- and transverse electric-polarized light and/or the phase difference between the transverse magnetic- and transverse electric-polarized light. Diffraction patterns themselves may be calculated for example using reflection coefficients.

Thus, although embodiments of the present invention are described in relation to reflective scattering, the invention is also applicable to transmissive scattering.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

REFERENCES

[1] Evgeny Popov and Michel Nevière. Maxwell equations in Fourier space: fast-converging formulation for diffraction by arbitrary shaped, periodic, anisotropic media. *J. Opt. Soc. Am. A,* 18(11):2886-2894, November 2001.

[2] I. S. Gradshteyn and I. M. Ryzhik. *Table of Integrals, Series and Products.* Academic Press, 1980.

[3] Thomas Schuster, Johannes Ruoff, Norbert Kerwien, Stephan Rafler, and Wolfgang Osten. Normal vector method for convergence improvement using the RCWA for crossed gratings. *J. Opt. Soc. Am. A,* 24(9):2880-2890, September 2007.

[4] R. V. Churchill. *Complex Variables and Applications.* McGraw-Hill, 1960.

[5] Peter Götz, Thomas Schuster, Karsten Frenner, Stephan Rafler, and Wolfgang Osten. Normal vector method for the RCWA with automated vector field generation. *OPTICS EXPRESS,* 16(22):17295-17301, October 2008.

[6] Alvise Sommariva and Marco Vianello. Gauss-Green cubature and moment computation over arbitrary geometries. *Journal of Computational and Applied Mathematics,* to be published.

[7] Alvise Sommariva and Marco Vianello. Product Gauss cubature over polygons based on Green's integration formula. *BIT Numerical Mathematics,* 47(2):147-177, August 2007.

[8] G. Gabard. Exact integration of polynomial-exponential products with application to wave-based numerical methods. *Commun. Numer. Meth. Engng,* 2008.

[9] Yia-Chung Chang, Guangwei Li, Hanyou Chu, and Jon Opsal. Efficient finite-element, Green's function approach for critical-dimension metrology of three-dimensional gratings on multilayer films. *J. Opt. Soc. Am. A,* 23(3):638-6454, March 2006.

[10] Lifeng Li. Use of Fourier series in the analysis of discontinuous periodic structures. *J. Opt. Soc. Am. A,* 13(9): 1870-1876, September 1996.

[11] Lifeng Li. New formulation of the Fourier modal method for crossed surface-relief gratings. *J. Opt. Soc. Am. A,* 14(10):2758-2767, October 1997.

[12] Brent C. Bergner, Thomas A. Germer, and Thomas J. Suleski. Effect of Line Width Roughness on Optical Scatterometry Measurements. Metrology, Inspection, and Process Control for Microlithography XXIII, edited by John A. Allgair, Christopher J. Raymond. *Proc. of SPIE Vol.* 7272, 72720U, 2009. DOI: 10.1117/12.813770.

APPENDIX A

Radial Integrals of Bessel Functions

The radial integration amounts to finding closed expressions for the following integrals $$\int z' J_{2n}(z')dz' \text{ and } \int z' J_{2n+1}(z')dz' \text{ for } (n \geq 0). \tag{A1}$$

These can be found by employing the following recurrence relations for Bessel functions ([2])

$$zJ_{n-1}(z) + zJ_{n+1}(z) = 2nJ_n(z), \tag{A2}$$

$$J_{n-1}(z) - J_{n+1}(z) = 2\frac{dJ_n(z)}{dz}. \tag{A3}$$

Substituting $n+1 \equiv 2k$ in Eq. (2) and integrating gives a recursive relation for the even Bessel integral $$\int zJ_{2k}(z)dz = 2(2k-1)\int J_{2k-1}(z)dz - \int zJ_{2k-2}(z)dz. \tag{A4}$$

The second integral in this equation can be rewritten using Eq. (A3). Substituting $n+1=2k-1$ and integrating gives $$\int J_{2k-1}(z')dz' = \int J_{2k-3}(z')dz' - 2J_{2k-2}(z). \tag{A5}$$

Both recursive integral expressions can be explicitly written $$\int^z z' J_{2k}(z')dz' = \quad (A6)$$

$$(-1)^k z J_1(z) + 2\sum_{m=1}^{k}(-1)^{k-m}(2m-1)\int^z J_{2m-1}(z')dz',$$

$$\int^z J_{2k-1}(z')dz' = -J_0(z) - 2\sum_{m=1}^{k-1} J_{2m}(z). \quad (A7)$$

Substitution of Eq. (A7) in Eq. (A6) gives $$\int^z z' J_{2n}(z')dz' = (-1)^n z J_1(z) - \quad (A8)$$

$$2J_0(z)\sum_{k=1}^{n}(-1)^{n-k}(2k-1) - 4\sum_{k=2}^{n}(-1)^{n-k}(2k-1)\sum_{m=1}^{k-1} J_{2m}(z).$$

The disadvantage of this expression is that the Bessel function has multiple evaluations of the same argument. Since this is numerically an expensive operation, the double summation is switched giving $$\int^z z' J_{2n}(z')dz' = (-1)^n z J_1(z) - 2(-1)^n J_0(z)\sum_{k=1}^{n}(-1)^k(2k-1) - \quad (A9)$$

$$4(-1)^n \sum_{m=1}^{n-1} J_{2m}(z) \sum_{k=m+1}^{n}(-1)^k(2k-1).$$

The last summation over the k-index can be shown to be equal to $$\sum_{k=m+1}^{n}(-1)^k(2k-1) = (-1)^n n - (-1)^m m, \quad (A10)$$

giving the final closed-form expression for the radial integral over the even Bessel functions $$\int^z z' J_{2n}(z')dz' = \quad (A11)$$

$$-2nJ_0(z) + (-1)^n z J_1(z) - 4\sum_{m=1}^{n-1} J_{2m}(z)[n-(-1)^{n-m}m],$$

where the summation only applies to n>1.

The same reasoning can be applied to the radial integral over the odd Bessel functions. Substituting n+1≡2k+1 in Eq. (A2) and n+1≡2k in Eq. (A3) and integrating gives the following recursive integrals $$\int^z z' J_{2k+1}(z')dz' = 2(2k)\int^z J_{2k}(z')dz' - \int^z z' J_{2k-1}(z')dz', \quad (A12)$$

$$\int^z J_{2k}(z')dz' = \int^z J_{2k-2}(z')dz' - 2J_{2k-1}(z). \quad (A13)$$

Writing both recursive relations explicitly gives $$\int^z z' J_{2n+1}(z')dz' = \quad (A14)$$

$$(-1)^n \int^z z' J_1(z')dz' + 2\sum_{k=1}^{n}(-1)^{n-k} 2k \int^z J_{2k}(z')dz',$$

$$\int^z J_{2n}(z')dz' = \int^z J_0(z')dz' - 2\sum_{k=1}^{n} J_{2k-1}(z). \quad (A15)$$

Substituting Eq. (A15) in Eq. (A14) and swapping the double summation gives $$\int^z z' J_{2n+1}(z')dz' = (-1)^n \int^z z' J_1(z')dz' + \quad (A16)$$

$$4\int^z J_0(z')dz' \sum_{k=1}^{n}(-1)^{n-k}k - 8\sum_{m=1}^{n} J_{2m-1}(z)\sum_{k=m}^{n}(-1)^{n-k}k.$$

Using the relation $$\sum_{k=m}^{n}(-1)^{n-k}k = \frac{1}{2}\left[\left(n+\frac{1}{2}\right) + (-1)^{n-m}\left(m-\frac{1}{2}\right)\right], \quad (A17)$$

and partially integrating $zJ_1(z)$ in Eq. (A16) gives the final expression $$\int^z z' J_{2n+1}(z')dz' = (2n+1)\int^z J_0(z')dz' + \quad (A18)$$

$$(-1)^{n+1} z J_0(z) - 2\sum_{m=1}^{n} J_{2m-1}(z)[(2n+1) + (-1)^{n-m}(2m-1)],$$

where the final summation only applies to n≥1.

APPENDIX B

Angular Integrals

The angular integral in its most general form is written as $$\int_0^{\varphi_s} \left\{ \begin{array}{c} e^2\cos^2\varphi \\ e\sin\varphi\cos\varphi \\ \sin^2\varphi \end{array} \right\} \frac{1}{e^2\cos^2\varphi + \sin^2\varphi} \left\{ \begin{array}{c} 1 \\ \cos[2k(\varphi-c)] \\ \cos[(2k+1)(\varphi-c)] \end{array} \right\} d\varphi, \quad (B1)$$

where all combinations of the terms between the curly brackets are possible, $$\left(0 < e = \frac{b}{a} < 1\right)$$

is the ellipticity, $\phi_s$ is the angle of the ellipse or circle segment and c is an angle offset following from geometrical input parameters (see Eq. (83)). Although a closed expression for this integral can be derived, we shall focus for this report on two particular cases,
 the circle segment
 the full ellipse
For the circle e=1 which substantially simplifies the integrals $$\begin{Bmatrix} \Phi_{xx}^{e/o} \\ \Phi_{xy}^{e/o} \\ \Phi_{yy}^{e/o} \end{Bmatrix} = \int_0^{\varphi_s} \begin{Bmatrix} \cos^2\varphi \\ \sin\varphi\cos\varphi \\ \sin^2\varphi \end{Bmatrix} \begin{Bmatrix} \cos[2k(\varphi-c)] \\ \cos[(2k+1)(\varphi-c)] \end{Bmatrix} d\varphi, \quad (B2)$$

where e refers to the even modes and o to the odd modes. Furthermore, all combinations of terms between the curly brackets are possible. Straightforward integration gives $$\Phi_{xx}^e(k, 0, \varphi_s) = \frac{1}{8(k-1)}(\sin[2(k-1)\varphi_s - 2kc] + \sin(2kc)) + \quad (B3)$$
$$= \frac{1}{4k}(\sin[2k\varphi_s - 2kc] + \sin(2kc)) +$$
$$\frac{1}{8(k+1)}(\sin[2(k+1)\varphi_s - 2kc] + \sin(2kc))$$
$$= \frac{1}{2}\left[\varphi_s + \frac{1}{2}\sin(2\varphi_s)\right](k=0) = \frac{1}{4}\varphi_s\cos(2c) + \quad (B4)$$
$$\frac{1}{4}[\sin(2\varphi_s - 2c) + \sin(2c)] + \quad (B5)$$
$$\frac{1}{16}[\sin(4\varphi_s - 2c) + \sin(2c)](k=1)$$

$$\Phi_{xy}^e(k, 0, \varphi_s) = \frac{1}{8(k-1)}(\cos[2(k-1)\varphi_s - 2kc] - \cos(2kc)) - \quad (B6)$$
$$\frac{1}{8(k+1)}(\cos[2(k+1)\varphi_s - 2kc] - \cos(2kc))$$
$$= \frac{1}{4}\varphi_s\sin(2c) - \frac{1}{16}[\cos(4\varphi_s - 2c) - \cos(2c)](k=1) \quad (B7)$$

$$\Phi_{yy}^e(k, 0, \varphi_s) = \frac{-1}{8(k-1)}(\sin[2(k-1)\varphi_s - 2kc] + \sin(2kc)) + \quad (B8)$$
$$\frac{1}{4k}(\sin[2k\varphi_s - 2kc] + \sin(2kc)) -$$
$$\frac{1}{8(k+1)}(\sin[2(k+1)\varphi_s - 2kc] + \sin(2kc))$$
$$= \frac{1}{2}\left[\varphi_s - \frac{1}{2}\sin(2\varphi_s)\right](k=0) \quad (B9)$$
$$= -\frac{1}{4}\varphi_s\cos(2c) + \frac{1}{4}[\sin(2\varphi_s - 2c) + \sin(2c)] - \quad (B10)$$
$$\frac{1}{16}[\sin(4\varphi_s - 2c) + \sin(2c)](k=1).$$

Similar expressions can be derived for the odd angular integrals $$\Phi_{xx}^o(k, 0, \varphi_s) = \quad (B11)$$
$$\frac{1}{4(2k-1)}(\sin[(2k-1)\varphi_s - (2k+1)c] + \sin[(2k+1)c]) +$$
$$\frac{1}{2(2k+1)}(\sin[(2k+1)\varphi_s - (2k+1)c] + \sin[(2k+1)c]) +$$
$$\frac{1}{4(2k+3)}(\sin[(2k+3)\varphi_s - (2k+1)c] + \sin[(2k+1)c]).$$

$$\Phi_{xy}^o(k, 0, \varphi_s) = \quad (B12)$$
$$\frac{1}{4(2k-1)}(\cos[(2k-1)\varphi_s - (2k+1)c] - \cos[(2k+1)c]) -$$
$$\frac{1}{4(2k+3)}(\cos[(2k+3)\varphi_s - (2k+1)c] - \cos[(2k+1)c]).$$

$$\Phi_{yy}^o(k, 0, \varphi_s) = \quad (B13)$$
$$\frac{-1}{4(2k-1)}(\sin[(2k+1)\varphi_s - (2k+1)c] + \sin[(2k+1)c]) +$$
$$\frac{1}{2(2k+1)}(\sin[(2k+1)\varphi_s - (2k+1)c] + \sin[(2k+1)c]) -$$
$$\frac{1}{4(2k+3)}(\sin[(2k+3)\varphi_s - (2k+1)c] + \sin[(2k+1)c]).$$

For the case of the full ellipse, e is arbitrary in Eq. (B1). The even angular integral $\Phi_{xx}^e(k, 0, 2\pi)$ can be written $$\Phi_{xx}^e(k, 0, 2\pi) = \int_0^{2\pi} \frac{e^2\cos^2\varphi}{e^2\cos^2\varphi + \sin^2\varphi}\cos[2k(\varphi-c)]d\varphi = \quad (B14)$$
$$\frac{e^2}{e^2+1}\cos(2kc)\frac{1}{2}\int_0^{4\pi}\left(\frac{1+\cos(u)}{1+a\cos(u)}\right)\cos(ku)du +$$
$$\frac{e^2}{e^2+1}\sin(2kc)\frac{1}{2}\int_0^{4\pi}\left(\frac{1+\cos(u)}{1+a\cos(u)}\right)\sin(ku)du \quad (u \equiv 2\varphi).$$

where the double-angle trigonometric relations have been used to rewrite the squares of the sines and cosines. Further use of the sine-cosine product rules and the fact that all trigonometric function have $2\pi$ periodicity, gives $$\Phi_{xx}^e(k, 0, 2\pi) = \frac{e^2}{e^2+1}\cos(2kc) \quad (B15)$$
$$\int_0^{2\pi}\left(\frac{\frac{1}{2}\cos[(k-1)u] + \cos(ku) + \frac{1}{2}\cos[(k+1)u]}{1+a\cos(u)}\right)du + \frac{e^2}{e^2+1}\sin(2kc)$$
$$\int_0^{2\pi}\left(\frac{\frac{1}{2}\sin[(k-1)u] + \sin(ku) + \frac{1}{2}\sin[(k+1)u]}{1+a\cos(u)}\right)du.$$

Exploiting the symmetries of the integrands, it can be shown that $$\int_0^{2\pi}\frac{\sin(ku)}{1+a\cos(u)}du = 0, \quad (B16)$$
$$\int_0^{2\pi}\frac{\cos(ku)}{1+a\cos(u)}du = 2(-1)^k\int_0^\pi\frac{\cos(kv)}{1-a\cos(v)}dv$$
$$= \frac{\pi}{\sqrt{1-a^2}}\left(\frac{\sqrt{1-a^2}-1}{-a}\right)^k (a^2 < 1), \quad (B17)$$

where an elementary integral has been used in Eq. (B17) (see [2, p. 366]). With the same symmetry arguments, it can be shown that $$\Phi_{xx}^o(k, 0, 2\pi) = \int_0^{2\pi}\frac{e^2\cos^2\varphi}{e^2\cos^2\varphi + \sin^2\varphi}\cos[(2k+1)(\varphi-c)]d\varphi = 0. \quad (B18)$$

Patiently repeating this work for $\Phi_{xy}^{e/o}$ and $\Phi_{yy}^{e/o}$ shows that $$\Phi_{xy}^o(k, 0, 2\pi) = \Phi_{yy}^o(k, 0, 2\pi) = 0, \quad (B19)$$

$$\begin{Bmatrix} \Phi_{xx}^e(k, 0, 2\pi) \\ \Phi_{xy}^e(k, 0, 2\pi) \\ \Phi_{yy}^e(k, 0, 2\pi) \end{Bmatrix} = \begin{Bmatrix} \frac{2\pi e}{(1+e)^2}\cos(2kc)\left(\frac{1-e}{1+e}\right)^{k-1} \\ \frac{2\pi e}{(1+e)^2}\sin(2kc)\left(\frac{1-e}{1+e}\right)^{k-1} \\ -\frac{2\pi e}{(1+e)^2}\cos(2kc)\left(\frac{1-e}{1+e}\right)^{k-1} \end{Bmatrix} \quad (B20)$$

$$= \begin{Bmatrix} \frac{2\pi e}{1+e} \\ 0 \\ \frac{2\pi}{1+e} \end{Bmatrix} \text{ (for } k = 0\text{).} \quad (B21)$$

Note that for the case of a circle (e=1) only the (k=1)-terms are non-zero.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method of calculating electromagnetic scattering properties of a structure, the structure including materials of differing properties such as to cause a discontinuity in an electromagnetic field at a material boundary, the method comprising:
    generating, using a processing device, a localized normal-vector field in a region of the structure defined with reference to the material boundary;
    constructing, using the processing device, a vector field that is continuous at the material boundary by using the normal-vector field to select continuous components of the electromagnetic field tangential to the material boundary and to select continuous components of a corresponding electromagnetic flux density normal to the material boundary;
    performing, using the processing device, a localized integration of the normal-vector field over the region to determine coefficients of a field-material interaction operator;
    numerically determining, using the processing device, a component of the electromagnetic field by using the field-material interaction operator to operate on the vector field; and
    calculating, using the processing device, electromagnetic scattering properties of the structure using the determined component of the electromagnetic field.

2. The method of claim 1, wherein the region corresponds to support of a contrast source.

3. The method of claim 1, wherein the step of generating the localized normal-vector field comprises sealing at least one of the continuous components.

4. The method of claim 3, wherein the scaling is configured to make the continuous components of the electromagnetic field and the continuous components of the electromagnetic flux density indistinguishable outside the region.

5. The method of claim 4, wherein the step of scaling comprises using a scaling function that is continuous at the material boundary.

6. The method of claim 1, wherein the step of generating the localized normal-vector field comprises using a transformation operator directly on the vector field to transform the vector field from a basis dependent on the normal-vector field to a basis independent of the normal-vector.

7. The method of claim 6, wherein the basis independent of the normal-vector field is a basis of the electromagnetic field and the electromagnetic flux density.

8. The method of claim 1, wherein the step of generating a localized normal-vector field comprises decomposing the region into a plurality of sub-regions each having a respective normal-vector field and the step of performing a localized integration comprises integrating over each the respective normal-vector field of each of the sub-regions.

9. The method of claim 8, wherein each sub-region is an elementary shape selected to have a respective normal-vector field having a corresponding closed-form integral and the step of performing a localized integration comprises using the corresponding closed-form integral for integrating over each the respective normal-vector field of each of the sub-regions.

10. The method of any claim 1, wherein the step of calculating electromagnetic scattering properties of the structure is performed by numerically solving a volume integral equation for the vector field, so as to determine an approximate solution of the vector field.

11. The method of claim 10, wherein the vector field is related to the electromagnetic field by a change of basis.

12. The method according to claim 11, wherein the vector field is represented by at least one finite Fourier series with respect to at least one direction and wherein the step of numerically solving the volume integral equation comprises determining a component of the electromagnetic field by convolution of the vector field with a convolution-and-change-of-basis operator.

13. The method of claim 1, further comprising relating the electromagnetic flux density to the electromagnetic field using, in the region in which the localized normal vector field is generated and local to the material boundary, a component of permittivity normal to the material boundary and at least one other, different, component of permittivity tangential to the material boundary.

14. A method of reconstructing an approximate structure of an object from a detected electromagnetic scattering property arising from illumination of the object by radiation, the method comprising the steps:
  estimating, using a processing device, at least one structural parameter;
  determining, using the processing device, at least one model electromagnetic scattering property from the at least one structural parameter;
  comparing, using the processing device, the detected electromagnetic scattering property to the at least one model electromagnetic scattering property; and
  determining, using the processing device, an approximate object structure based on the result of the comparison,
  wherein the model electromagnetic scattering property is determined using a method of calculating electromagnetic scattering properties of a structure, the structure including materials of differing properties such as to cause a discontinuity in an electromagnetic field at a material boundary, the method comprising:
  generating, using the processing device, a localized normal-vector field in a region of the structure defined with reference to the material boundary;
  constructing, using the processing device, a vector field that is continuous at the material boundary by using the normal-vector field to select continuous components of the electromagnetic field tangential to the material boundary and to select continuous components of a corresponding electromagnetic flux density normal to the material boundary;
  performing, using the processing device, a localized integration of the normal-vector field over the region to determine coefficients of a field-material interaction operator;
  numerically determining, using the processing device, a component of the electromagnetic field by using the field-material interaction operator to operate on the vector field; and
  calculating, using the processing device, electromagnetic scattering properties of the structure using the determined component of the electromagnetic field.

15. An inspection apparatus for reconstructing an approximate structure of an object, the inspection apparatus comprising:
  an illumination system configured to illuminate the object with radiation;
  a detection system configured to detect an electromagnetic scattering property arising from the illumination:
  a processor configured to:
  estimate at least one structural parameter;
  determine at least one model electromagnetic scattering property from the at least one structural parameter;
  compare the detected electromagnetic scattering property to the at least one model electromagnetic scattering property; and
  determine an approximate object structure from a difference between the detected electromagnetic scattering property and the at least one model electromagnetic scattering property,
  wherein the processor is configured to determine the model electromagnetic scattering property using of calculating electromagnetic scattering properties of a structure, the structure including materials of differing properties such as to cause a discontinuity in an electromagnetic field at a material boundary, the method comprising:
  generating a localized normal-vector field in a region of the structure defined with reference to the material boundary;
  constructing a vector field that is continuous at the material boundary by using the normal-vector field to select continuous components of the electromagnetic field tangential to the material boundary and to select continuous components of a corresponding electromagnetic flux density normal to the material boundary;
  performing a localized integration of the normal-vector field over the region to determine coefficients of a field-material interaction operator;
  numerically determining a component of the electromagnetic field by using the field-material interaction operator to operate on the vector field; and
  calculating electromagnetic scattering properties of the structure using the determined component of the electromagnetic field.

16. A non-transitory computer program product containing one or more sequences of machine-readable instructions for calculating electromagnetic scattering properties of a structure, the instructions being adapted to cause one or more processors to perform a method of calculating electromagnetic scattering properties of a structure, the structure including materials of differing properties such as to cause a discontinuity in an electromagnetic field at a material boundary, the method comprising:
  generating a localized normal-vector field in a region of the structure defined with reference to the material boundary;
  constructing a vector field that is continuous at the material boundary by using the normal-vector field to select continuous components of the electromagnetic field tangential to the material boundary and to select continuous components of a corresponding electromagnetic flux density normal to the material boundary;
  performing a localized integration of the normal-vector field over the region to determine coefficients of a field-material interaction operator;
  numerically determining a component of the electromagnetic field by using the field-material interaction operator to operate on the vector field; and
  calculating electromagnetic scattering properties of the structure using the determined component of the electromagnetic field.

17. A method comprising:
  generating, using a processing device, a localized normal vector field in a region of a structure defined with reference to a material boundary;
  constructing, using the processing device, a vector field that is continuous at the material boundary by using the normal vector field to select continuous components of an electromagnetic field tangential to the material boundary and to select continuous components of a corresponding electromagnetic flux density normal to the material boundary;

performing, using the processing device, a localized integration of the normal vector field over the region to determine coefficients of a field material interaction operator;

numerically determining, using the processing device, a component of the electromagnetic field by using the field material interaction operator to operate on the vector field; and calculating, using the processing device, electromagnetic scattering properties of the structure using the determined component of the electromagnetic field.

18. The method of claim 17, wherein the generating the localized normal vector field comprises scaling at least one of the continuous components.

19. The method of claim 18, wherein the scaling is configured to make the continuous components of the electromagnetic field and the continuous components of the electromagnetic flux density indistinguishable outside the region.

20. The method of claim 19, wherein the scaling comprises using a scaling function that is continuous at the material boundary.

21. The method of claim 20, wherein the scaling further comprises using a scaling operator that is continuous at the material boundary.

22. The method of claim 17, wherein the generating the localized normal vector field comprises using a transformation operator directly on the vector field to transform the vector field from a basis dependent on the normal vector field to a basis independent of the normal vector field.

23. The method of claim 22, wherein the basis independent of the normal vector field is a basis of the electromagnetic field and the electromagnetic flux density.

24. The method of claim 17, wherein the calculating electromagnetic scattering properties of the structure is performed by numerically solving a volume integral equation for the vector field, so as to determine an approximate solution of the vector field.

25. The method of claim 24, wherein the vector field is related to the electromagnetic field by a change of basis.

26. The method of claim 17, further comprising relating the electromagnetic flux density to the electromagnetic field using, in the region in which the localized normal vector field is generated and local to the material boundary, a component of permittivity normal to the material boundary and at least one other, different, component of permittivity tangential to the material boundary.

27. A method comprising:
estimating, using a processing device, at least one structural parameter;
determining, using the processing device, at least one model electromagnetic scattering property from the at least one structural parameter;
comparing, using the processing device, a detected electromagnetic scattering property to the at least one model electromagnetic scattering property; and
determining, using the processing device, an approximate object structure based on a result of the comparison,
wherein the model electromagnetic scattering property is determined by:
generating, using the processing device, a localized normal vector field in a region of a structure defined with reference to a material boundary;
constructing, using the processing device, a vector field that is continuous at the material boundary by using the normal vector field to select continuous components of an electromagnetic field tangential to the material boundary and to select continuous components of a corresponding electromagnetic flux density normal to the material boundary;
performing, using the processing device, a localized integration of the normal vector field over the region to determine coefficients of a field material interaction operator;
numerically determining, using the processing device, a component of the electromagnetic field by using the field material interaction operator to operate on the vector field; and
calculating, using the processing device, electromagnetic scattering properties of the structure using the determined component of the electromagnetic field.

28. An inspection apparatus comprising:
an illumination system configured to illuminate an object with radiation;
a detection system configured to detect an electromagnetic scattering property arising from the illumination; and
a processor configured to:
estimate at least one structural parameter;
determine at least one model electromagnetic scattering property from the at least one structural parameter;
compare the detected electromagnetic scattering property to the at least one model electromagnetic scattering property; and
determine an approximate object structure from a difference between the detected electromagnetic scattering property and the at least one model electromagnetic scattering property,
wherein the processor is configured to determine the model electromagnetic scattering property by:
generating a localized normal vector field in a region of a structure defined with reference to a material boundary;
constructing a vector field that is continuous at the material boundary by using the normal vector field to select continuous components of an electromagnetic field tangential to the material boundary and to select continuous components of a corresponding electromagnetic flux density normal to the material boundary;
performing a localized integration of the normal vector field over the region to determine coefficients of a field material interaction operator;
numerically determining a component of the electromagnetic field by using the field material interaction operator to operate on the vector field; and
calculating electromagnetic scattering properties of the structure using the determined component of the electromagnetic field.

29. A non-transitory computer program product containing one or more sequences of machine-readable instructions for calculating electromagnetic scattering properties of a structure, the instructions being adapted to cause one or more processors to perform a method, the method comprising:
generating a localized normal vector field in a region of a structure defined with reference to a material boundary;
constructing a vector field that is continuous at the material boundary by using the normal vector field to select continuous components of an electromagnetic field tangential to the material boundary and to select continuous components of a corresponding electromagnetic flux density normal to the material boundary;
performing a localized, integration of the normal vector field over the region to determine coefficients of a field material interaction operator;

numerically determining a component of the electromagnetic field by using the field material interaction operator to operate on the vector field; and calculating electromagnetic scattering properties of the structure using the determined component of the electromagnetic field.

* * * * *

UNITED STATES PATENT AND TRADEMARK OFFICE
CERTIFICATE OF CORRECTION

PATENT NO.        : 8,706,455 B2  
APPLICATION NO.   : 12/905447  
DATED             : April 22, 2014  
INVENTOR(S)       : Van Beurden et al.

Page 1 of 1

It is certified that error appears in the above-identified patent and that said Letters Patent is hereby corrected as shown below:

In the Claims

Column 52, line 28, claim 3, delete "sealing" and insert --scaling--  
Column 55, line 59, claim 27, delete ";" and insert --:--

Signed and Sealed this  
Second Day of September, 2014

Michelle K. Lee  
*Deputy Director of the United States Patent and Trademark Office*